(12) United States Patent  
Araoka

(10) Patent No.: US 8,941,682 B2
(45) Date of Patent: Jan. 27, 2015

(54) MEDICAL IMAGE PROCESSING APPARATUS AND INFORMATION RETRIEVAL APPARATUS

(75) Inventor: Junichiro Araoka, Nasushiobara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 272 days.

(21) Appl. No.: 13/520,597

(22) PCT Filed: Oct. 28, 2011

(86) PCT No.: PCT/JP2011/006054
§ 371 (c)(1),
(2), (4) Date: Jul. 5, 2012

(87) PCT Pub. No.: WO2012/063426
PCT Pub. Date: May 18, 2012

(65) Prior Publication Data
US 2012/0274657 A1    Nov. 1, 2012

(30) Foreign Application Priority Data

Nov. 8, 2010  (JP) .................................. 2010-249651

(51) Int. Cl.
*G09G 5/00* (2006.01)
*G06F 19/00* (2011.01)
(Continued)

(52) U.S. Cl.
CPC ........ *G06F 19/322* (2013.01); *G06F 17/30247* (2013.01); *G06F 17/30991* (2013.01);
(Continued)

(58) Field of Classification Search
CPC ............ G09G 5/00; G09G 5/08; G06F 3/048; G06F 17/30; G06F 3/01; G06F 3/16; G06Q 50/22; G06Q 50/24

USPC ......................................................... 345/619
See application file for complete search history.

(56) References Cited

U.S. PATENT DOCUMENTS 5,129,074 A * 7/1992 Kikuchi et al. ............... 711/173
5,781,905 A * 7/1998 Awane et al. ..................... 1/1
(Continued)

FOREIGN PATENT DOCUMENTS

| JP | 2004 318766 | 11/2004 |
|---|---|---|
| JP | 2007 34457 | 2/2007 |
| JP | 2008 77573 | 4/2008 |

OTHER PUBLICATIONS

International Search Report Issued Jan. 17, 2012 in PCT/JP11/006054 Filed Oct. 28, 2011.

*Primary Examiner* — David Zarka
*Assistant Examiner* — Brian Kravitz
(74) *Attorney, Agent, or Firm* — Oblon, Spivak, McClelland, Maier & Neustadt, L.L.P.

(57) ABSTRACT

The retrieval of medical data from a database through easy operations without displaying components for retrieval operations on a display screen is realized. The present invention is a medical image processing apparatus comprising a data memory, a display, a position-designating part, a data-list-display controller, and a keyword-generating part. The data memory stores medical data associated with attributes data including patient identification information. The position-designating part designates a position on the display. The data-list-display controller causes the display to display a data list presenting the attributes data in a list. The keyword-generating part generates a retrieval key based on the attributes data in the data list corresponding to the position designated by the position-designating part. Moreover, the data-list-display controller updates the data list based on the results retrieved by the retrieval key.

9 Claims, 18 Drawing Sheets

(51) Int. Cl.
*G06F 17/30* (2006.01)
*G06Q 50/24* (2012.01)

(52) U.S. Cl.
CPC .......... *G06Q50/24* (2013.01); *G06F 17/30268* (2013.01); *G06F 17/30696* (2013.01); *G06F 19/321* (2013.01)
USPC ...................................................... 345/619

(56) References Cited

U.S. PATENT DOCUMENTS

| | | | |
|---|---|---|---|
| 7,535,477 B2* | 5/2009 | Zaima et al. | 345/619 |
| 2002/0080150 A1* | 6/2002 | Nakatani | 345/660 |
| 2003/0222925 A1* | 12/2003 | Regelous | 345/856 |
| 2004/0153343 A1* | 8/2004 | Gotlib et al. | 705/3 |
| 2005/0075906 A1* | 4/2005 | Kaindl et al. | 705/2 |
| 2005/0076024 A1* | 4/2005 | Takatsuka et al. | 707/3 |
| 2005/0091615 A1* | 4/2005 | Suzuki | 715/863 |
| 2005/0102166 A1* | 5/2005 | Tohma | 705/3 |
| 2009/0007174 A1* | 1/2009 | Fukuda et al. | 725/39 |
| 2009/0048874 A1* | 2/2009 | Sasano | 705/3 |
| 2009/0254557 A1* | 10/2009 | Jordan | 707/9 |
| 2009/0282492 A1* | 11/2009 | Takahashi | 726/27 |
| 2009/0322692 A1* | 12/2009 | Kim et al. | 345/173 |
| 2010/0235484 A1* | 9/2010 | Bolan et al. | 709/223 |
| 2011/0087651 A1* | 4/2011 | Westin et al. | 707/722 |
| 2011/0137620 A1* | 6/2011 | Kawabe et al. | 703/1 |

* cited by examiner

FIG. 2

|  | PATIENT ID | PATIENT NAME | AGE | EXAMINATION DATE/TIME [FEB-2010] | DIAGNOSED SITE |
|---|---|---|---|---|---|
|  | AA01 | YAMADA TARO | 23 | FEB-15, 2010 | HEAD |
|  | AA02 | YAMAMOTO JIRO | 34 | FEB-14, 2010 | BREAST |
|  | AB12 | TANAKA HIROYUKI | 45 | FEB-10, 2010 | ABDOMEN |
|  | ... | ... | ... | ... | ... |

VIEW

FIG. 3

|  | PATIENT ID | PATIENT NAME | AGE | EXAMINATION DATE/TIME | DIAGNOSED SITE |
|---|---|---|---|---|---|
|  | AA01 | YAMADA TARO | 23 | FEB-15, 2010 | HEAD |
|  | AA02 | YAMAMOTO JIRO | 34 | FEB-14, 2010 | BREAST |
|  | AB12 | TANAKA HIROYUKI | 45 | FEB-10, 2010 | ABDOMEN |
|  | ... | ... | ... | ... | ... |
|  |  |  |  | [FEB-2010] |  |

VIEW

| PATIENT ID | PATIENT NAME | AGE | EXAMINATION DATE/TIME [FEB-2010] | DIAGNOSED SITE |
|---|---|---|---|---|
| AA01 | YAMADA TARO | 23 | *FEB-15, 2010* | HEAD |
| AA02 | YAMAMOTO JIRO | 34 | *FEB-14, 2010* | BREAST |
| AB12 | TANAKA HIROYUKI | 45 | *FEB-10, 2010* | ABDOMEN |
| ... | ... | ... | ... | ... |

VIEW

MEDICAL IMAGE PROCESSING APPARATUS AND INFORMATION RETRIEVAL APPARATUS

CROSS-REFERENCE TO RELATED APPLICATIONS

This application is based upon and claims the benefit of priority from Japanese Patent Applications No. 2010-249651, filed Nov. 8, 2010; the entire contents of all of which are incorporated herein by reference.

FIELD

Embodiments of the present invention are related to technology for retrieving medical data in a medical image processing apparatus that stores multiple items of medical data.

BACKGROUND

Medical image processing apparatuses are known as devices (or systems) that manage and store medical data such as medical records and medical images. Medical data are created for individual patients and diagnoses. Therefore, a medical image processing apparatus must store large amounts of medical data in a readable manner.

To make it possible to identify and read out individual items of these medical data, these medical data are correlated with multiple attributes and stored in a database. Attributes include patient information such as patient ID, name and birthday or history information such as the date and time of creation or the date and time of imaging. The medical data stored in the database are read out using retrieval conditions. By designating suitable retrieval conditions, the operator narrows down the medical data read out from the database.

Conventionally, these retrieval conditions are input as character strings in a prescribed input field using a keyboard. However, to extract desired medical data using this method, it is necessary to accurately input a search formula corresponding to the system. Moreover, because search formulas differ between systems, it is necessary for operators to learn methods of designating search formulas corresponding to the system in advance.

As a method of resolving problems such as that described above, technology that makes it possible to input retrieval conditions using a displayed GUI (Graphical User Interface) has been proposed. As a result of this technology, it has become possible for operators to designate retrieval conditions through simple operations without designating any complex search formulas. However, this technology requires a dedicated operation means for inputting retrieval conditions on the display screen to be displayed on the screen. Therefore, the practical use of this technology requires a wide screen.

The embodiments of the present invention are designed to resolve the above problems, and the objective is to realize the retrieval of medical data from a database storing large amounts of medical data through simple operations.

BRIEF DESCRIPTION OF THE DRAWINGS

FIG. 2 is an example of a screen displayed on the display.
FIG. 3 is an example of an operation screen.

DETAILED DESCRIPTION

Figure 1:
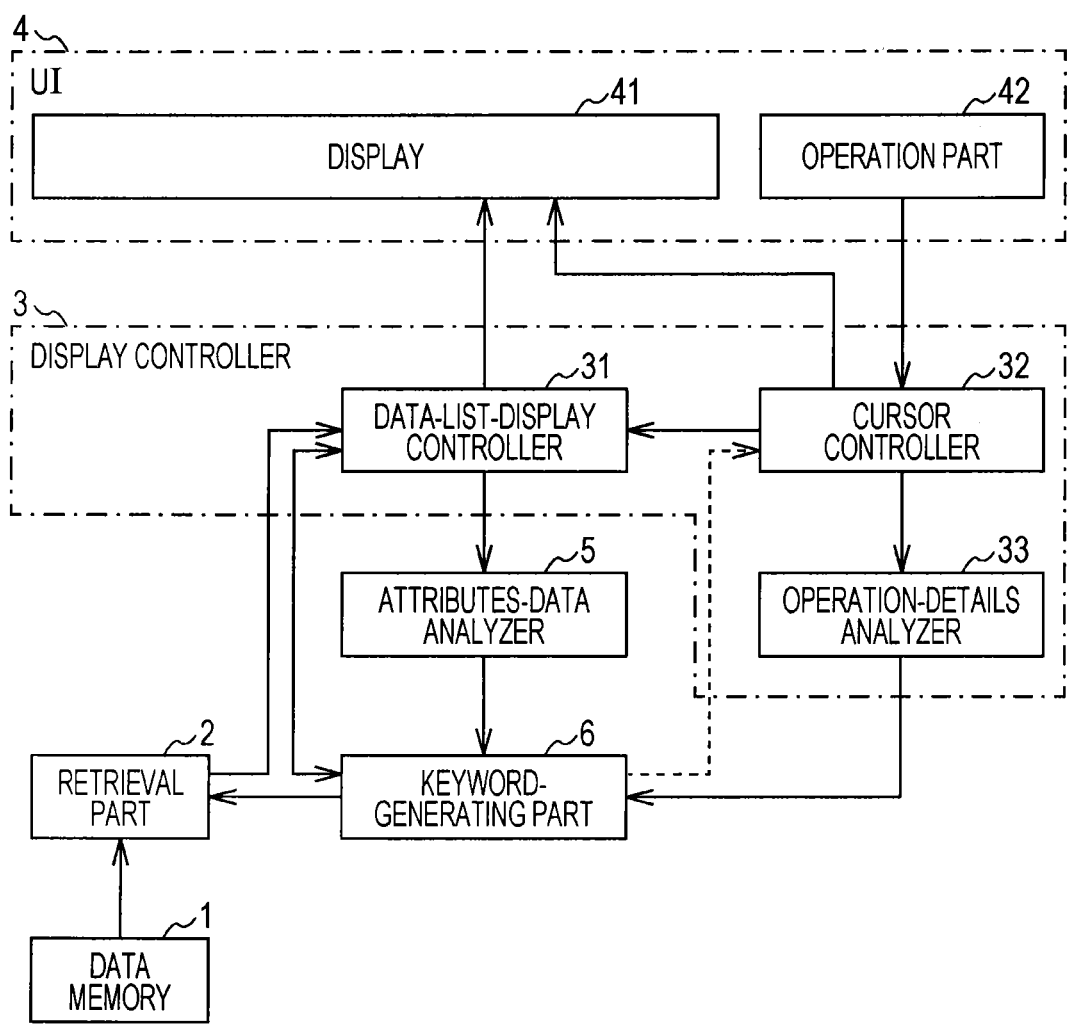
FIG. 1 is a block diagram of a medical image processing apparatus according to the first embodiment, the second embodiment, and the fourth embodiment.

To achieve the above objective, the first mode of the present embodiment is a medical image processing apparatus including a data memory, a display, a position-designating part, a data-list-display controller, and a keyword-generating part. The data memory stores medical data associated with attributes data including patient identification information. The position-designating part designates a position on the display. The data-list-display controller causes the display to display a data list presenting the attributes data in a list. The keyword-generating part generates a retrieval key based on the attributes data in the data list corresponding to the position designated by the position-designating part. Moreover, the data-list-display controller updates the data list based on the results retrieved by the retrieval key.

Moreover, the second mode of the present embodiment is a medical image processing apparatus including an operation part, a display, a data memory, a data-list-display controller, a cursor controller, an attributes-data analyzer, a keyword-generating part, and a retrieval part. The data memory stores medical data associated with attributes data represented as one or multiple units of data. The data-list-display controller associates a data list presenting the attributes data in a list with position information on the display, and displays the data list on the display. The cursor controller displays a cursor on the display and, upon receiving an instruction from the operation part, changes the position at which the cursor is displayed and outputs the position information thereof. The attributes-data analyzer identifies units of data within the attributes data based on the position information. The keyword-generating part changes the selection range of the units of data within the attributes data in conjunction with changes in the position information, and generates a retrieval key based on the units of data corresponding to the selection range. The retrieval part searches the data memory using the retrieval key. Moreover, the data-list-display controller receives the retrieval results of the retrieval part and updates and displays the data list.

Moreover, the third mode of the present embodiment is an information retrieval apparatus including a user interface part, a controller, a data memory, a data-list-display controller, an attributes-data analyzer, an operation-details analyzer, a keyword-generating part, and a retrieval part. The user interface part includes an operation part and a display. The controller outputs position information representing a position on the display designated by the operation part. The data memory stores retrieval-object data associated with attributes data represented as one or multiple units of data. The data-list-display controller causes the display to display a data list presenting attributes data associated with the retrieval-object data stored in the memory in a list. The attributes-data analyzer receives the position information from the controller, identifies the attributes data associated with the position information from within the data list as operation object data, and divides the operation object data into the units of data. Based on the position information, the operation-details analyzer detects the direction of movement and amount of movement of the position designated by the operation part. If the direction of movement detected by the operation-details analyzer includes components along a predetermined first axis, the keyword-generating part extracts a number of the units of data corresponding to the components from the operation object data and generates a retrieval key. The retrieval part searches the data memory using the retrieval key. Moreover, the data-list-display controller receives the retrieval results of the retrieval part and updates and displays the data list.

(First Embodiment)

The configuration of the medical image processing apparatus according to the first embodiment will now be described with reference to FIG. 1. Although it is possible to use this medical image processing apparatus as a device that searches a general relational database, the example of searching a medical-information database storing medical data will be set forth.

The medical image processing apparatus is configured by a data memory 1, a retrieval part 2, a display controller 3, a UI (User Interface) 4, an attributes-data analyzer 5, and a keyword-generating part 6. Moreover, the display controller 3 includes a data-list-display controller 31, a cursor controller 32, and an operation-details analyzer 33. Moreover, the UI 4 includes a display 41 and an operation part 42.

The data memory 1 is configured as a database. In the data memory 1, multiple items of medical data are stored in an identifiable and readable manner. Medical data refers to records created by physicians during diagnoses and data collected during examinations of patients. Examples of medical data include written records such as electronic charts and radiogram interpretation reports, as well as image data such as medical images. In describing the configuration of the medical image processing apparatus according to the present embodiment, first, the structure of the data stored within the data memory 1 will be described.

(Data structure)

The medical data are associated with one or more attributes and stored in the data memory 1. Attributes refer to data for identifying each item of medical data stored in the data memory 1. Examples of types of attributes include patient information and imaging information. Patient information includes, for example, patient ID, the first and last names of a patient, the birthday of a patient, and the sex of a patient. Moreover, imaging information includes, for example, the imaging region and the date of imaging. In the following description, the data names of attributes such as "last name" and "first name" may be referred to simply as "attributes." Moreover, values set for each attribute may be referred to as "attributes data." For example, for the attribute of "sex", the attributes data is either "male" or "female."

The attributes data are configured by one or more prescribed units of data (hereinafter also referred to as "units of data"). The units of data are the smallest item of data defined in advance for each item of attributes data. For example, if an item of attributes data is character string data, the units of data are character data. Specifically, if an item of attributes data is the character string "ABCD", this item of attributes data is configured by the units of data "A", "B", "C", and "D". Moreover, if an item of attributes data is a date, the "year", "month", and "day" may each be units of data. In this way, a configuration may be used in which the units of data may be defined according to the type of attributes data. In this case, it is preferable to define the units of data according to the data type of the attributes data. Data types refer to the data types of the database. For example, if an item of attributes data is a character string, examples of the data type of this attribute include a fixed-length character string format and a variable-length character string format. Moreover, the definitions of the units of data may be stored in a separate storage region. In this case, it is preferable to cause the configuration that identifies the units of data to refer to this storage region. In the following description, the units of data are defined according to the data type of the attributes data.

The medical image processing apparatus according to the present embodiment displays a list of the attributes data described above on the display 41. The medical image processing apparatus receives cursor operations performed on the list of attributes data. In response to these cursor operations, the medical image processing apparatus updates the data list displayed on the display 41 or causes the display 41 to display a desired item of medical data. In the following description, the use of a mouse will be described as an example of a cursor operation. Cursor operations include "operations to change the position of the cursor," "operations to select a position on the display 41," and "operation to select a start point and end point on the display 41." A start point refers to a position on the display 41 indicating the point where an operation is started. Moreover, an end point refers to a position on the display 41 where an operation is ended. An operation to change the position of the cursor refers to, for example, an operation to move the mouse. Moreover, an operation to select a position on the display 41 refers to, for example, a click operation. A click operation refers to an operation in which a button on the mouse is pressed without moving the mouse. Moreover, an operation to select a start point and end point on the display 41 refers to, for example, a drag operation. The drag operation refers to an operation of moving the mouse with the button on the mouse pressed. In the following description, cursor operations will be described by being associated with "operations to move the mouse," "click operations," and "drag operations" as described above. Furthermore, in the following description, configurations related to each operation will be described by being divided into "displaying of an operation screen," "creation of retrieval conditions," and "displaying of medical data." Furthermore, configurations for performing cursor operations, such as a mouse, correspond to the "position-designating part."

(Displaying of an Operation Screen)

First, configurations related to the displaying of an operation screen will be described. The retrieval part 2 and the data-list-display controller 31 operate to display an operation screen. The retrieval part 2 reads out a list of attributes data from the data memory 1. The data-list-display controller 31 forms this list of attributes data in a tabular form and creates a data list. The data-list-display controller 31 creates an operation screen based on the created data list. In the following description, the operations of the retrieval part 2 and the data-list-display controller 31 will first be described. Then, the screen configuration of the operation screen will be described.

(Retrieval Part 2)

Based on an instruction from the keyword-generating part 6, the retrieval part 2 searches the data memory 1 and reads out either a list of attributes data or medical data from the data memory 1. The following is a description of operations related to searches of lists of attribute data and searches of medical data that are executed by the retrieval part 2. The keyword-generating part 6 will be described later.

First, operations related to a search of a list of attributes data will be described. The retrieval part 2 receives an instruction related to the reading out of a list of attributes data from the keyword-generating part 6. In this case, the retrieval part 2 searches the data memory 1 and reads out a list of attributes data associated with various medical data from the data memory 1. If this instruction is accompanied by a designation of retrieval conditions by the keyword-generating part 6, the retrieval part 2 reads out only a list of attributes data associated with medical data matching the retrieval conditions from the data memory 1. The retrieval part 2 outputs the list of attributes data to the data-list-display controller 31.

Next, operations related to a search of medical data will be described. The retrieval part 2 receives an instruction related to the reading out of medical data together with retrieval conditions from the keyword-generating part 6. In this case, the retrieval part 2 searches the data memory 1 and reads out medical data matching the retrieval conditions from the data memory 1. The retrieval part 2 outputs the medical data to the data-list-display controller 31.

(Data-list-display controller 31)

The data-list-display controller 31 receives the list of attributes data from the retrieval part 2. The data-list-display controller 31 forms the list of attributes data in a tabular form and creates a data list C1. The data-list-display controller 31 incorporates the created data list C1 into a predetermined display format and creates an operation screen 41*a*. The data-list-display controller 31 causes the display 41 to display the created operation screen 41*a*. In this case, the data-list-display controller 31 associates the various operation means configuring the operation screen 41*a* (e.g., the data list C1, or a data reference means C2 described below) with position information on the display 41. As a result, the data-list-display controller 31 becomes able to identify an operation object designated on the operation screen 41*a* based on position information on the display 41. FIG. 2 shows an example in which the operation screen 41*a* and a cursor 41*b* (not shown in FIG. 2—shown for example in FIG. 4) for designating an operation object on the operation screen 41*a* are displayed on the display 41. In this case, the data-list-display controller 31 preferably identifies the operation object based on the position information of the cursor 41*b*. The screen configuration of the operation screen 41*a* will be described later. In the following, an example in which the cursor 41*b* is operated through a cursor operation will be described.

Moreover, the data-list-display controller 31 receives medical data from the retrieval part 2. The data-list-display controller 31 causes the display 41 to display this medical data. In this case, the data-list-display controller 31 may be configured to cause the medical data to be displayed according to a predetermined display format.

(Screen Configuration of the Operation Screen 41*a*)

Next, the screen configuration of the operation screen 41*a* will be described with reference to FIG. 3. FIG. 3 shows an example of the operation screen 41*a*. As shown in FIG. 3, the operation screen 41*a* includes the data list C1 and the data reference means C2.

On the data list C1, the attributes that are display objects and the attributes data of those attributes are displayed in a tabular form. The following is a detailed description of the data list C1. The data list C1 includes a region C11 and a region C12. In the region C11, each attribute is arranged and displayed in a predetermined sequence. Moreover, in the region C12, each item of attributes data is arranged and displayed. In this case, each item of attributes data associated with a single item of medical data is arranged and displayed in a single row in the same sequence as each attribute displayed in the region C11. In other words, the rows and medical data are associated with each other on a 1:1 basis. In the region C12, these rows are arranged in the row direction, the number of these rows being determined by the number of items of medical data matching the retrieval conditions. In this case, the data-list-display controller 31 associates each item of attributes data with position information on the display 41. As a result, when the operation screen 41*a* is operated using the cursor 41*b* (not shown in FIG. 3), etc., it is possible to identify the attributes data of the operation object based on the position information on the display 41. If there are too many rows to be displayed in a single screen, as shown in FIG. 3, a scrollbar C12*a* may be displayed.

The data reference means C2 is an operation means for displaying medical data. When the data reference means C2 is operated while a row is selected, the retrieval part 2 reads out the medical data corresponding to the selected row. The data-list-display controller 31 causes the display 41 to display the read-out medical data, allowing the operator to identify and refer to desired medical data based on the data list C1.

Figures 4, 5:
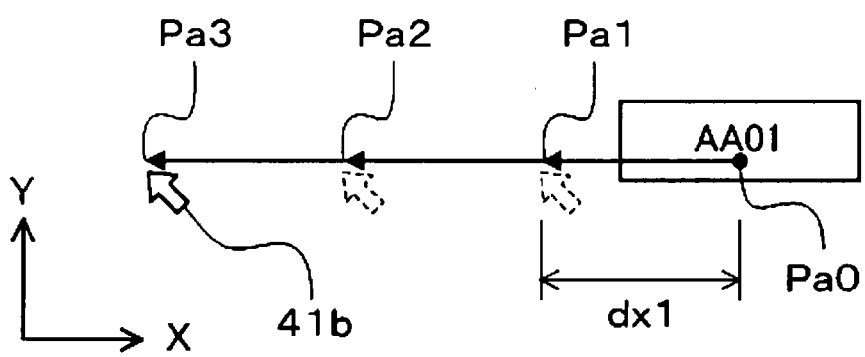
FIG. 4 is an example of an operation screen.
FIG. 5 is a diagram for describing an example of operations during a drag operation.

If retrieval conditions are designated when reading out the list of attributes data, the retrieval part 2 may cause the retrieval conditions to be displayed on the operation screen 41*a*. For example, as shown in FIG. 3, a configuration may be used in which the retrieval conditions designated at the time of retrieval are displayed together with the attributes that are the object of those retrieval conditions (e.g., the position of C11*a* in FIG. 2). Moreover, the operation screen 41*a* shown in FIG. 4 is a different example of the operation screen 41*a* shown in FIG. 3. As shown in FIG. 3, a region C3 that displays designated retrieval conditions may be provided separately. In this case, the data-list-display controller 31 may provide an associated field within the region C3 for each attribute, and may cause the retrieval conditions to be displayed within the fields associated with the attributes that are the object of the retrieval conditions (e.g., the position of C3*a* in FIG. 3). Moreover, as with the attributes data of "examination date and time" shown in FIG. 2, for each item of attributes data displayed in the region C12, the part to which the retrieval conditions have been applied may be emphasized and displayed. The method of emphasis may be, for example, displaying by changing the color, or displaying by changing the font using italics or bolding, etc.

(Creation of Retrieval Conditions)

Next, configurations related to the creation of retrieval conditions will be described. When creating retrieval conditions, mainly, the operation part 42, the cursor controller 32, the data-list-display controller 31, the attributes-data analyzer 5, and the keyword-generating part 6 operate. In the following, the configurations of the operation part 42 related to cursor operations as well as the cursor controller 32 will first be described. Then, operations of the data-list-display controller 31, the attributes-data analyzer 5, and the keyword-generating part 6 will be described.

(Operation Part 42)

Using the operation part 42, the operator performs a cursor operation on the operation screen 41a to instruct the medical image processing apparatus to perform a process. The operation part 42 outputs information indicating the details of the cursor operation performed by the operator (hereinafter also referred to as "operation information") to the cursor controller 32. The operation information includes operations for moving the mouse, click operations, and drag operations.

(Cursor Controller 32)

In addition to causing the cursor 41b to be displayed on the display 41, the cursor controller 32 also acquires position information (e.g., coordinates within the display 41) indicating the position where the cursor 41b is displayed. Moreover, when the cursor 41b is operated by the operation part 42, the cursor controller 32 executes the various processes indicated below in accordance with the details of the operation.

If the mouse has been moved, the cursor controller 32 changes the position of the cursor 41b on the display 41 in accordance with the movement operation. Moreover, if the position of the cursor 41b has been changed, the cursor controller 32 acquires the position information of the cursor 41b again.

If a mouse button has been pressed (specifically, if a click operation has been performed or if a drag operation has been started), the cursor controller 32 outputs the position information of the cursor 41b at that time point to the data-list-display controller 31. This click operation and drag operation are associated with operations for selecting an operation object (e.g., attributes data). Therefore, the data-list-display controller 31 identifies the attributes data selected as the operation object based on the position information.

If a drag operation has been performed, the cursor controller 32 detects the start of a drag operation based on signals from the operation part 42. In this case, the cursor controller 32 outputs the position information of the cursor 41b at the start of the drag operation (i.e., the start point) to the operation-details analyzer 33. Moreover, each time the position of the cursor 41b is changed during the drag operation, the cursor controller 32 outputs the position information of the cursor 41b to the operation-details analyzer 33. Moreover, if the drag operation ends and the end point is determined (if the mouse button being pressed has been released), the cursor controller 32 detects the end of the drag operation based on signals from the operation part 42. In this case, the cursor controller 32 notifies the operation-details analyzer 33 of the end of the drag operation. The cursor controller 32 may change the shape of the cursor 41b depending on the position of the cursor 41b and the details of the operation performed on the cursor 41b. As an example, if the cursor 41b is positioned in a specific region, the cursor controller 32 may change the shape of the cursor 41b. As another example, the cursor controller 32 may change the shape of the cursor 41b during the drag operation.

Next, the configurations of the data-list-display controller 31, the attributes-data analyzer 5, and the keyword-generating part 6 will be described. The medical image processing apparatus according to the present embodiment creates retrieval conditions based on the operation information of a drag operation as well as the attributes data that are the operation object. In the following, operations of each configuration will be described with a focus on operations performed during a drag operation. Operations performed during a click operation will be described together with configurations related to the "displaying of medical data."

(Operation-Details Analyzer 33)

Based on the position information of the start point and the position information of the cursor 41b, the operation-details analyzer 33 calculates a vector from the start point toward the position of the cursor 41b. Next, the operation-details analyzer 33 calculates information indicating the vertical-axis components (hereinafter also referred to as "vertical-axis components") and information indicating the horizontal-axis components (hereinafter also referred to as "horizontal-axis components") of the calculated vector. The vertical-axis components include information indicating the direction along the vertical axis (up or down) and information indicating the amount of movement along the vertical axis. Moreover, the horizontal-axis components include information indicating the direction along the horizontal axis (left or right) and the amount of movement along the horizontal axis. The operation-details analyzer 33 is able to calculate the abovementioned vertical-axis components and horizontal-axis components by, for example, comparing the sizes of the position information (coordinates) of the start point and the position information (coordinates) of the cursor 41b. For example, if the coordinates of the start point in the horizontal axis are greater than the coordinates of the cursor 41b in the horizontal axis, the operation-details analyzer 33 indicates left as the direction along the horizontal axis. Moreover, if the coordinates of the start point in the vertical axis are less than the coordinates of the cursor 41b in the vertical axis, the operation-details analyzer 33 indicates up as the direction along the vertical axis.

The operation-details analyzer 33 outputs the calculated vertical-axis components and horizontal-axis components to the keyword-generating part 6. Moreover, if the drag operation ends, the operation-details analyzer 33 notifies the keyword-generating part 6 of the end of the drag operation. As a result, the keyword-generating part 6 is able to identify the position of the cursor 41b at the time of the end of the drag operation as the end point. In the following descriptions, if an X-axis and a Y-axis are shown on a diagram, the X-axis corresponds to the horizontal axis and the Y-axis corresponds to the vertical axis.

(Data-List-Display Controller 31)

When a drag operation is started, the data-list-display controller 31 receives the position information of the start point from the cursor controller 32. The data-list-display controller 31 identifies the attributes data associated with the position information of the start point as the operation object data. The data-list-display controller 31 outputs the identified operation object data to the attributes-data analyzer 5.

(Attributes-Data Analyzer 5)

Based on the data type of the identified operation object data, the attributes-data analyzer 5 divides the operation object data into units of data. For example, if the operation object data are the character string "AA1", the attributes-data analyzer 5 divides the operation object data into the units of data "A", "A", "0", and "1". The attributes-data analyzer 5 outputs the operation object data that has been divided into units of data to the keyword-generating part 6 while maintaining the order in which the units of data are arranged.

(Keyword-generating part 6)

The keyword-generating part 6 according to the present embodiment creates retrieval conditions based on the horizontal-axis components and the operation object data received from the operation-details analyzer 33. The keyword-generating part 6 reads out the information indicating the direction along the horizontal axis included in the horizontal-axis components, and creates different retrieval conditions depending on whether the direction is left or right. First, operations performed when the direction along the horizontal axis is left will be described, and then operations performed when the direction is right will be described next. The horizontal axis corresponds to the "first axis." In this case, left corresponds to the "first direction," and right corresponds to the "second direction."

(If the direction along the horizontal axis is left)

If the direction along the horizontal axis is left, the keyword-generating part 6 creates retrieval conditions (hereinafter also referred to as "suitable conditions") for extracting only rows matching prescribed conditions. The rows matching prescribed conditions refer to rows in which attributes data including all or part of the operation object data have been set for attributes of the same type as the operation object data. In the following description, data indicating all or part of the operation object data may be referred to as "partial data." For example, if the operation object data is "AA01," examples of partial data include "A", "AA," "AA0," and "AA01." Operations of the keyword-generating part 6 will be described below with reference to FIG. 5. The position Pa0 in FIG. 5 indicates the position of the start point. Moreover, the position Pa1 indicates the position located to the left of the position Pa0 and separated by a predetermined unit distance dx1. Similarly, the position Pa2 indicates the position separated from the position Pa0 by the distance 2dx1. Moreover, the position Pa3 indicates the position separated from the position Pa0 by the distance 3dx1.

The keyword-generating part 6 first divides the information indicating the amount of movement that is included in the horizontal-axis components (i.e., "the amount of movement in the leftward direction") by the unit distance dx1. Then, the keyword-generating part 6 defines positions along the horizontal axis as shown in FIG. 5 (e.g., the positions Pa1 -Pa3). If the amount of movement in the leftward direction is shorter than the unit distance dx1 (i.e., if the cursor 41b is positioned between Pa0 and Pa1), the keyword-generating part 6 uses the unit of data positioned at the head of the operation object data (hereinafter also referred to as "head data") as the partial data. As shown in FIG. 5, if the operation object data is "AA01" the keyword-generating part 6 defines the partial data as "A".

Each time the amount of movement in the leftward direction increases by the unit distance dx1, the keyword-generating part 6 extracts a unit of data in the direction from the head of the operation object data to the tail. The keyword-generating part 6 combines the extracted unit of data with the tail of the partial data. For example, if the cursor 41b is positioned between the position Pa1 and the position Pa2, the partial data become "AA" as the head data "A" and the subsequent unit of data "A" are combined. Similarly, if the cursor 41b is positioned between the position Pa2 and the position Pa3, the partial data become "AA0," and if the cursor 41b is positioned to the left of the position Pa3, the partial data become "AA01."

If the drag operation is continued further to the left while the partial data are the operation object data, the keyword-generating part 6 does not update the partial data. In other words, if the cursor 41b is moved further left from the position Pa3, the partial data remain "AA01" regardless of the amount of movement thereof. Moreover, each time the amount of movement in the leftward direction decreases by the unit distance dx1, the keyword-generating part 6 removes a unit of data from the tail of the partial data. For example, if the cursor 41b is moved from a position to the left of the position Pa3 to between the position Pa3 and the position Pa2, the keyword-generating part 6 updates the partial data from "AA01 " to "AA0."

Figure 6:
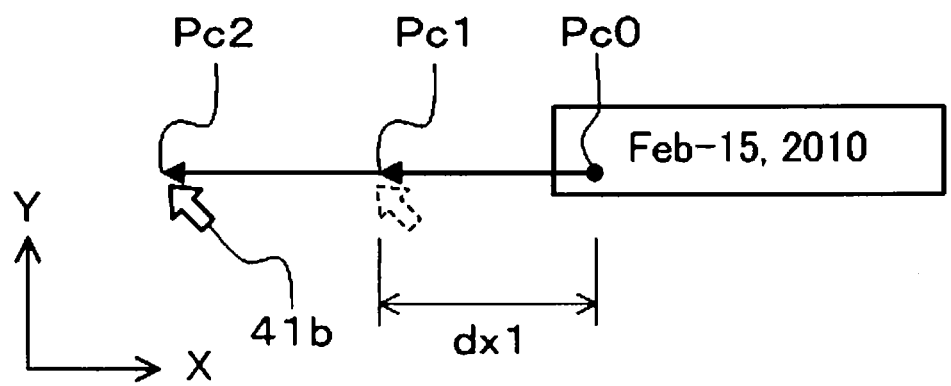
FIG. 6 is a diagram for describing an example of operations during a drag operation.

Moreover, as shown in FIG. 6, if the operation object data are data indicating a date and time, any of the "year," "month," or "day" may be processed as the head data. In this case, each time the amount of movement in the leftward direction increases by the unit distance dx1, it is preferable to add another unit of data. For example, as shown in FIG. 6, if the operation object data are the character sequence "Feb.-15, 2010" (Feb.15, "2010" ), the "2010" indicating the year is processed as the head data. In this case, if the cursor 41b is positioned between the position Pc0 and the position Pc1, the partial data become "2010."Then, a configuration may be used in which, each time the amount of movement increases by the unit distance dx1, units of data are combined with the partial data in the order of the "month" and "day." In other words, if the cursor 41b is positioned at the position Pc1, the partial data become "Feb.-2010." Moreover, if the cursor 41b is positioned at the position Pc2, the partial data become "Feb.-15, 2010."

When the partial data are updated, the keyword-generating part 6 creates suitable conditions based on the partial data. Specifically, the keyword-generating part 6 creates retrieval conditions for extracting rows in which attributes data that anteriorly match the partial data have been set for the same attributes as those of the operation object data. An anterior match refers to when the anterior part (the head side) of the attributes data matches the partial data. In this case, the retrieval key is generally expressed by attaching a "*" to the tail of the partial data. For example, if the partial data are "AA," the retrieval key is expressed as "AA*." If retrieval is performed using the retrieval key "AA*,"attributes data that start with "AA," such as the attributes data "AA01" and "AA12,"become the retrieval objects.

(If the Direction Along the Horizontal Axis is Right)

Next, operations performed when the direction along the horizontal axis is right will be described. In this case, retrieval conditions (hereinafter also referred to as "suitable conditions") for extracting only rows that do not match prescribed conditions are created. The rows that do not match prescribed conditions refer to rows in which attributes data that do not include all or part of the operation object data are set for the same attributes as those of the operation object data. In the following, operations of the keyword-generating part 6 will be described with reference to FIG. 7. The position Pb in FIG. 7 indicates the position of the start point. Moreover, the position Pb1 indicates a position to the right of the position Pb0 that is separated by the predetermined unit distance dx1 . Similarly, the position Pb indicates a position separated from the position Pb by the distance dx1. Moreover, the position Pb indicates a position separated from the position Pb by the distance dx1.

Figure 7:
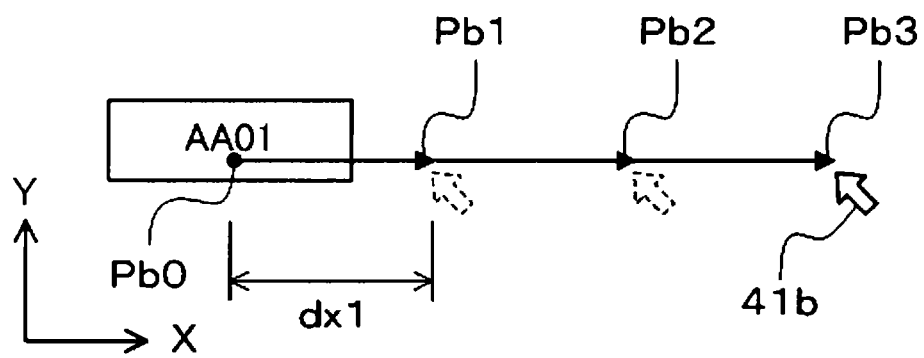
FIG. 7 is a diagram for describing an example of operations during a drag operation.

The keyword-generating part 6 first divides the information indicating the amount of movement that is included in the horizontal-axis components (i.e., "the amount of movement in the rightward direction") by the unit distance dx1. Then, the keyword-generating part 6 defines positions along the horizontal axis as shown in FIG. 7 (e.g., the positions Pb1- Pb3). If the amount of movement in the rightward direction is shorter than the unit distance dx1 (i.e., if the cursor 41b is positioned between the position Pb0 and the position Pb1), the keyword-generating part 6 uses the operation object data as partial data. For example, as shown in FIG. 7, if the operation object data are the character string "AA01," the keyword-generating part 6 defines the partial data as "AA01."

Each time the amount of movement in the rightward direction increases by the unit distance dx1, the keyword-generating part 6 removes a unit of data from the tail of the operation object data. For example, if the cursor 41b is positioned between the position Pb1 and the position Pb2, the unit of data "1" positioned at the tail of the partial data "AA01 " is removed to create "AA0." Similarly, if the cursor 41b is positioned between the position Pb2 and the position Pb3, the partial data become "AA," and if the cursor 41b is positioned to the right of the position Pb3, the partial data become "A".

If the drag operation is continued further to the right while the partial data are the head data of the operation object data, the keyword-generating part 6 does not update the partial data. In other words, if the cursor 41b is moved further to the right from the position Pb3, the partial data remain "A" regardless of the amount of movement thereof. Moreover, each time the amount of movement in the rightward direction decreases by the unit distance dx1, a removed unit of data is combined with the tail of the partial data. For example, if the cursor 41b is moved from a position to the right of the position Pb3 to between the position Pb3 and the position Pb2, the keyword-generating part 6 updates the partial data from "A" to "AA."

When the partial data are updated, the keyword-generating part 6 creates unsuitable conditions based on the partial data. Specifically, the keyword-generating part 6 creates retrieval conditions for extracting rows in which attributes data that anteriorly match the partial data have not been set for the same attributes as those in the operation object data. Unsuitable conditions are generally expressed by attaching a "!" to the head of the retrieval key. For example, if retrieval is performed using the retrieval key "!AA*," attributes data that start with "AA," such as the attributes data "AA01 " and "AA12," are removed from the retrieval object. In the following descriptions, the processes of creating retrieval conditions based on drag operations along the horizontal axis as described above may be referred to as "processes based on horizontal-axis components."

When retrieval conditions are created, the keyword-generating part 6 outputs the retrieval conditions to the data-list-display controller 31, allowing the data-list-display controller 31 to cause the retrieval conditions to be displayed on the operation screen 41a as shown in C11a in FIG. 3 or C3a in FIG. 4. Moreover, the keyword-generating part 6 may output the retrieval conditions to the cursor controller 32, allowing the cursor controller 32 to cause the retrieval conditions to be displayed on the side of the cursor 41b while following the operations of the cursor 41b, for example.

Once notified by the operation-details analyzer 33 of the end of the drag operation, the keyword-generating part 6 outputs the retrieval conditions created at that time point to the retrieval part 2. The retrieval part 2 receives the retrieval conditions and searches the data memory 1 based on the retrieval conditions. The data-list-display controller 31 receives the retrieval results and updates the data list. As a result, the drag operation of the operator is received, and the rows displayed on the data list are narrowed down in real time based on the retrieval conditions.

If retrieval conditions have already been created for the attributes of the operation object data and narrowing down has been performed, the keyword-generating part 6 may operate to create new retrieval conditions based on these retrieval conditions. For example, if a drag operation is performed in the leftward direction when narrowing down has been performed with the retrieval conditions "AA*," the partial data that act as the basis for creating retrieval conditions become "AA." The same applies for unsuitable conditions. In other words, if the cursor 41b is positioned between the positions Pa0 and Pa1 of FIG. 5, the partial data become "AA," and each time the cursor 4b is moved further by the unit distance dx1, the keyword-generating part 6 operates to combine a unit of data with the tail of the partial data.

In the following descriptions, the partial data when the amount of movement along the horizontal axis is less than the unit distance dx1 may be referred to as the "foundation of the partial data." For example, a case in which the operation object data are "AA01 " will be described. If narrowing down using retrieval conditions has not been performed, the foundation of the partial data during a drag operation in the leftward direction becomes "A", and the foundation of the partial data during a drag operation in the rightward direction becomes "AA01." Moreover, if narrowing down has been performed with the retrieval conditions "AA*, " the foundation of the partial data during a drag operation in the leftward direction becomes "AA." Moreover, if narrowing down has been performed with the retrieval conditions "!AA*," the foundation of the partial data during a drag operation in the rightward direction becomes "AA."

(Displaying of Medical Data)

Next, configurations related to the displaying of medical data will be described. When displaying medical data, mainly, the operation part 42, the cursor controller 32, the data-list-display controller 31, the keyword-generating part 6, and the retrieval part 2 operate. The operator selects a desired row from the data list displayed on the operation screen 41a by performing a click operation. Then, when the data reference means C2 is operated, medical data corresponding to the selected row are retrieved and displayed by the medical image processing apparatus. The following is a description of the operations of each configuration, with a focus on operations performed when a click operation has been performed.

(Cursor Controller 32)

If a click operation has been performed, the cursor controller 32 outputs the position information of the cursor 41b at that time point to the data-list-display controller 31.

(Data-List-Display Controller 31)

If the position information of the cursor 41b corresponds to a row in the data list, the data-list-display controller 31 sets that row to the selected state. In this case, the data-list-display controller 31 may cause the selected row to be displayed in an identifiable manner.

Moreover, if the position information of the cursor 41b corresponds to the data reference means C2, the data-list-display controller 31 confirms whether or not a row set to the selected state is present. If attributes data set to the selected state are present, the data-list-display controller 31 outputs each item of attributes data included in that row to the keyword-generating part 6. If no attributes data are set to the selected state, the data-list-display controller 31 may be configured to cause the display 41 to display a message prompting the operator to select a row.

(Keyword-Generating Part 6)

The keyword-generating part 6 receives each item of attributes data included in the selected row from the data-list-display controller 31. The keyword-generating part 6 creates retrieval conditions for extracting medical data associated with the received attributes data. The keyword-generating part 6 outputs the created retrieval conditions to the retrieval part 2.

(Retrieval Part 2)

The retrieval part 2 searches the data memory 1 based on the retrieval conditions and extracts the corresponding medical data. The retrieval part 2 outputs the extracted medical data to the data-list-display controller 31. The data-list-display controller 31 causes the display 41 to display this medical data. As a result, medical data corresponding to the selected row are displayed on the display 41.

Figure 8:
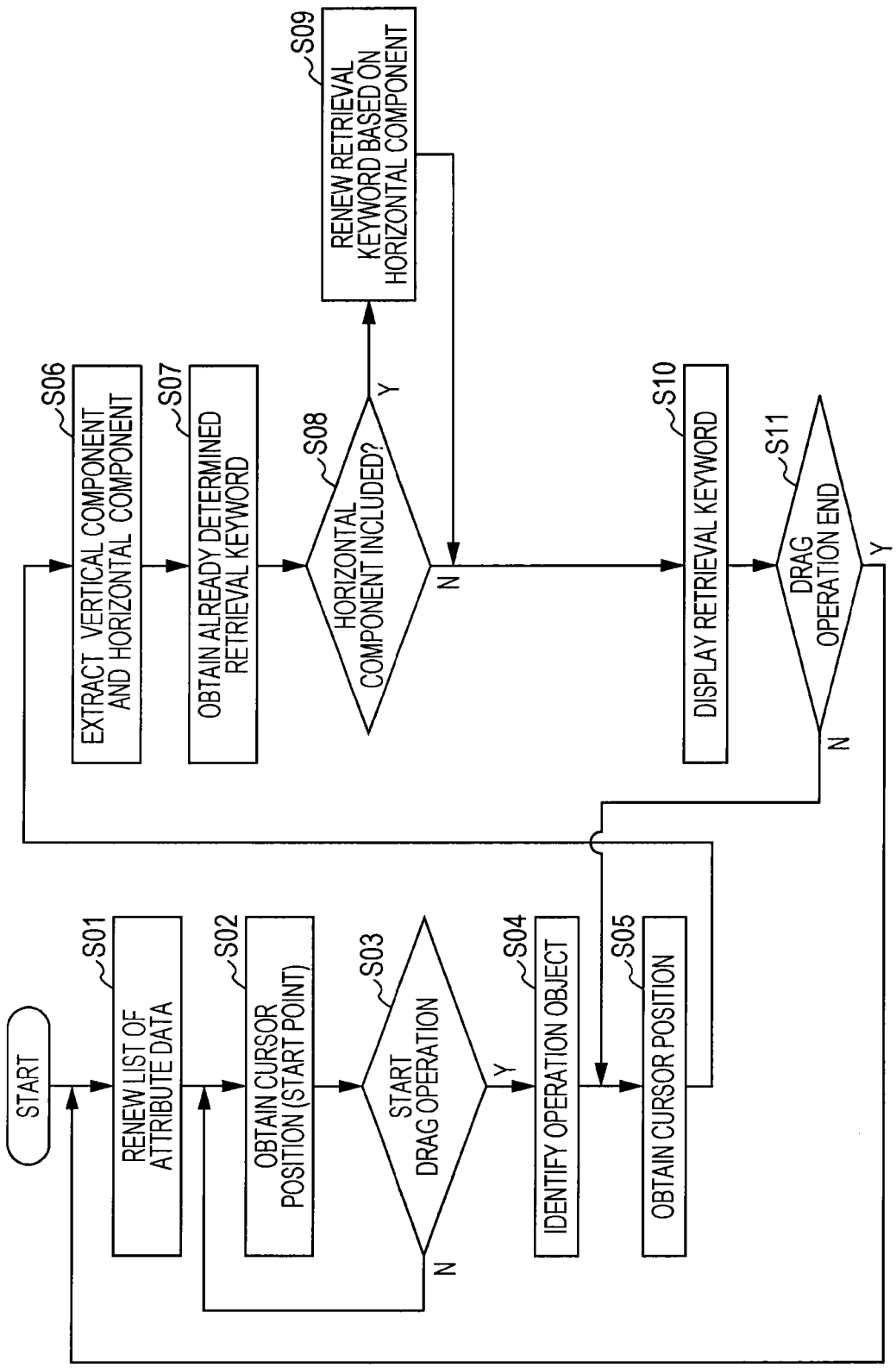
FIG. 8 is a flowchart of a medical image processing apparatus according to the first embodiment.

Next, a series of operations performed during a drag operation will be described with reference to FIG. 8. FIG. 8 is a flowchart showing operations performed by the medical image processing apparatus during a drag operation.

(Step S01)

When the operator executes an operation related to the retrieval of medical data, the retrieval part 2 that receives this operation searches the data memory 1 and reads out a list of attributes data. The retrieval part 2 outputs the list of attributes data that has been read out to the data-list-display controller 31. The data-list-display controller 31 forms the list of attributes data in a tabular form and creates the data list C1. The data-list-display controller 31 incorporates the created data list C1 into a predetermined display format and creates the operation screen 41a. The data-list-display controller 31 causes the display 41 to display the created operation screen 41a.

(Step S02)

When the operation screen 41a is displayed, the cursor controller 32 monitors the position of the cursor 41b and acquires the position information of the cursor 41b.

(Step S03)

When a drag operation is performed by the operator using attributes data displayed on the operation screen 41a as the start point (Step S03: Y), the cursor controller 32 outputs the position information of the start point to the data-list-display controller 31. When no drag operation is being performed (Step S03: N), the cursor controller 32 continues monitoring the position of the cursor 41b.

(Step S04)

The data-list-display controller 31 identifies the attributes data associated with the position information of the start point as the operation object data. The data-list-display controller 31 outputs the identified operation object data to the attributes-data analyzer 5. Based on the data type of the identified operation object data, the attributes-data analyzer 5 divides the operation object data into units of data. The attributes-data analyzer 5 outputs the operation object data that have been divided into units of data to the keyword-generating part 6 together with the order in which the units of data are arranged.

(Step S05)

Moreover, the cursor controller 32 acquires the position information of the cursor 41b. The cursor controller 32 outputs the position information of the start point and the position information of the cursor 41b to the operation-details analyzer 33.

(Step S06)

Based on the position information of the start point and the position information of the cursor 41b, the operation-details analyzer 33 calculates a vector from the start point toward the position of the cursor 41b. Next, the operation-details analyzer 33 calculates the vertical-axis components and horizontal-axis components of the calculated vector. The operation-details analyzer 33 outputs the calculated vertical-axis components and horizontal-axis components to the keyword-generating part 6.

(Step S07)

The keyword-generating part 6 confirms whether or not retrieval conditions have already been created for the attributes of the operation object data. If retrieval conditions have already been created, partial data that act as the foundation are generated based on the retrieval conditions. If retrieval conditions have not been created, partial data that act as the foundation are not generated at this time. In this case, the keyword-generating part 6 generates partial data that act as the foundation in accordance with the direction along the horizontal axis in the subsequent processes.

(Step S08)

Next, the keyword-generating part 6 confirms whether or not horizontal-axis components are included in the vector calculated by the operation-details analyzer 33.

(Step S09)

If horizontal-axis components are included in the vector (Step S08: Y), the keyword-generating part 6 creates retrieval conditions based on the horizontal-axis components and the operation object data. The keyword-generating part 6 creates different retrieval conditions depending on whether the direction of the horizontal-axis components is left or right. If the direction is left, the keyword-generating part 6 creates suitable conditions based on information indicating the amount of movement in the leftward direction that is included in the horizontal-axis components. Moreover, if the direction is right, the keyword-generating part 6 creates unsuitable conditions based on information indicating the amount of movement in the rightward direction that is included in the horizontal-axis components. If horizontal-axis components are not included in the vector (Step S08: N), these processes are not performed.

(Step S10)

Once the retrieval conditions are created, the keyword-generating part 6 outputs the retrieval conditions to the data-list-display controller 31. As a result, the data-list-display controller 31 becomes able to display the retrieval conditions on the operation screen 41a as shown in C11a of FIG. 3 or C3a of FIG. 4.

(Step S11)

If the drag operation is continuing (Step S11: N), the cursor controller 32 continues monitoring the position of the cursor 41b. Each time the position of the cursor 41b changes, the cursor controller 32 outputs the position information of the start point and the position information of the cursor 41b to the operation-details analyzer 33. When the drag operation ends (Step S11: Y), the operation-details analyzer 33 notifies the keyword-generating part 6 of the end of the drag operation. The keyword-generating part 6 receives the notification of the end of the drag operation and outputs the created retrieval conditions to the retrieval part 2.

(Step S01)

The retrieval part 2 searches the data memory 1 based on the retrieval conditions. The data-list-display controller 31 receives the retrieval results and updates the data list. As a result, upon receiving a drag operation performed by the operator, the rows displayed in the data list are narrowed down in real time based on the retrieval conditions. Subsequently, as long as operations performed by the operator continue, the medical image processing apparatus repeatedly executes the above processes. Upon detecting that operations have ended, the medical image processing apparatus ends the above processes by stopping the operations of each configuration.

The above description set forth an example of sequentially monitoring the position of the cursor to acquire position information, but the configurations may instead operate by accepting a cursor operation and acquiring position information. In this case, the operations of steps S02 and S03, for example, may be replaced with processes to receive the start of a drag operation and acquire the position information of the start point.

As described above, according to the medical image processing apparatus of the first embodiment, it becomes possible to create retrieval conditions based on a drag operation in the horizontal axis and to narrow down the rows displayed in a data list based on these retrieval conditions. As a result, it becomes possible to realize the retrieval of medical data from a database storing large amounts of medical data through simple operations without displaying a dedicated operation means for retrieval operations on the display screen.

(Second Embodiment)

Next, the medical image processing apparatus according to the second embodiment will be described. The keyword-generating part 6 according to the present embodiment creates retrieval conditions based on vertical-axis components during a drag operation. In this case, the keyword-generating part 6 may operate in combination with processes related to the creation of retrieval conditions based on the horizontal-axis components. The following is a description of the medical image processing apparatus according to the second embodiment, with a focus on configurations of the keyword-generating part 6 that differ from those of the medical image processing apparatus according to the first embodiment.

(Keyword-Generating Part 6)

The keyword-generating part 6 according to the present embodiment creates retrieval conditions based on vertical-axis components and the operation object data. In this case, based on information indicating a direction along the vertical axis and information indicating the amount of movement along the vertical axis, the keyword-generating part 6 changes the units of data positioned at the tail of the partial data configuring the retrieval conditions (hereinafter also referred to as "tail data") to create new retrieval conditions. Operations of the keyword-generating part 6 will be described with reference to FIG. 9, using an example in which "AA1 *" has already been designated for the retrieval conditions and the operation object data are "AA11". The position Pe0 in FIG. 9 indicates the position of the start point. Moreover, the position Pe1 indicates a position below the position Pe0 that is separated by the predetermined unit distance dy1. Similarly, the position Pe2 indicates a position separated from the position Pe0 by the unit distance 2dy1. Moreover, the position Pe3 indicates a position separated from the position Pe0 by the unit distance 3dy1.

Figure 9:
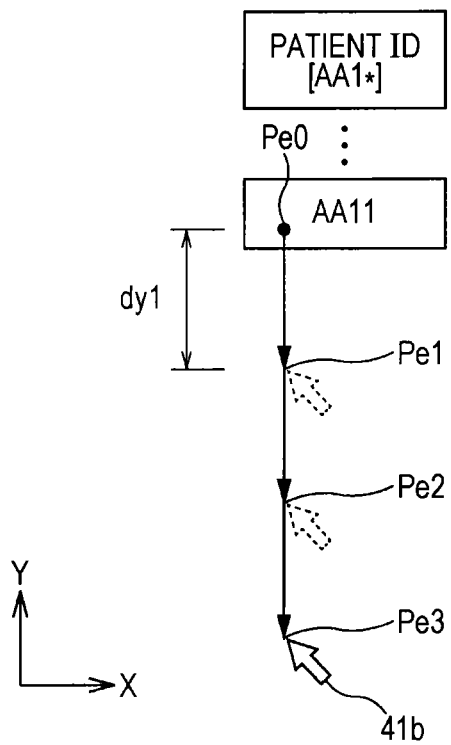
FIG. 9 is a diagram for describing an example of operations during a drag operation.

First, the keyword-generating part 6 identifies the tail data. In the case of FIG. 9, the foundation of the partial data is "AA1," and the tail of the partial data in this case is "1". Next, the keyword-generating part 6 creates a list of candidates for the post-change units of data in accordance with the identified tail data. For example, as shown in FIG. 9, if the tail data are numbers, the list of candidates preferably includes the numbers 0 through 9. Moreover, if the tail data are alphabetic characters, the list of candidates preferably includes the letters A through Z. In this way, the list of candidates is preferably created in accordance with the type of tail data. Further, the keyword-generating part 6 may refer to the data memory 1 to create a list of these candidates based on a list of attribute data set for the attribute. For example, it is supposed that for each item of medical data stored in the data memory 1, only one of the options "AA11," "AA12," or "AA22" is set for the attributes data. In this case, these medical data cannot be extracted using retrieval conditions in which the tail data "1" of the partial data "AA1" is changed to tail data other than "1" or "2". Therefore, it is also possible to cause the keyword-generating part 6 to operate to include only "1" and "2" in the list of candidates corresponding to the tail data "1" of the partial data "AA1."

The keyword-generating part 6 creates a scale in which the list of candidates is arranged in a predetermined and prescribed order. Then, the keyword-generating part 6 identifies the position of the tail data in the created scale. In the following description, the values 0 through 9 are arranged in ascending order on this scale. Next, the keyword-generating part 6 associates the direction along the vertical axis (up or down) with a direction on the scale. For example, the keyword-generating part 6 associates the direction in which the values on the scale decrease (descending direction) with the upward direction, and the direction in which the values on the scale increase (ascending direction) with the downward direction. The vertical axis corresponds to the "second axis." Moreover, downward in this case corresponds to the "third direction," and upward corresponds to the "fourth direction."

Moreover, the keyword-generating part 6 divides information indicating the amount of movement that is included in the vertical-axis components by the predetermined unit distance dy1. Then, the keyword-generating part 6 defines positions along the vertical axis (e.g., the positions Pe1 to Pe3) as shown in FIG. 9.

Next, each time the amount of movement included in the vertical-axis components increases by the unit distance dy1, in accordance with the order on the scale, the keyword-generating part 6 creates new retrieval conditions by changing the tail data of the retrieval conditions that have already been set. An example will be described in which the cursor 41 is positioned between the position Pe1 and the position Pe2 as shown in FIG. 9. The tail data in this case is "1". Moreover, the tail data "1" is immediately followed by "2" in the ascending order. Therefore, the keyword-generating part 6 newly creates the retrieval conditions "AA2*," in which the tail data of the retrieval conditions "AA1*" has been changed to "2". Similarly, if the cursor is positioned between the position Pe2 and the position Pe3, the keyword-generating part 6 newly creates the retrieval conditions "AA3*." Moreover, if the cursor 41b is positioned below the position Pe3, the keyword-generating part 6 newly creates the retrieval conditions "AA4*."

The keyword-generating part 6 outputs the retrieval conditions created based on the drag operation in the vertical-axis direction to the retrieval part 2. In this case, the keyword-generating part 6 may output the most recently created retrieval conditions to the retrieval part 2, or may output all or part of the created retrieval conditions to the retrieval part 2. For example, a case in which a drag operation has been performed to the position Pe2 will be described. If outputting the most recently created retrieval conditions to the retrieval part 2, the keyword-generating part 6 outputs only the retrieval conditions "AA3*" to the retrieval part 2. Moreover, if outputting all of the created retrieval conditions to the retrieval part 2, the keyword-generating part 6 outputs the retrieval conditions "AA1*," "AA2*," and "AA3*" to the retrieval part 2. In the following descriptions, the processes of creating retrieval conditions based on a drag operation along the vertical-axis direction as described above may be referred to as "processes based on vertical-axis components."

Figure 10:
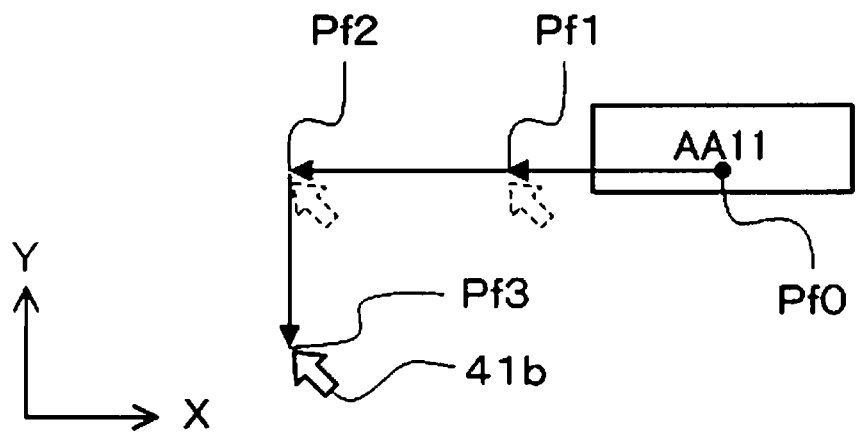
FIG. 10 is a diagram for describing an example of operations during a drag operation.

Moreover, as shown in FIG. 10, the keyword-generating part 6 may operate by combining the processes based on horizontal-axis components of the keyword-generating part 6 according to the first embodiment with the processes based on vertical-axis components described above. For example, if a drag operation exceeds the position Pf2 in the leftward direction, the keyword-generating part 6 creates the retrieval conditions "AA0 *" based on the processes based on horizontal-axis components. In this state, if a drag operation exceeds the position Pf3 in the downward direction, the keyword-generating part 6 creates the retrieval conditions "AA1 *" in addition to "AA0 *" based on the processes based on vertical-axis components.

It is not always necessary to make both the processes based on horizontal-axis components and the processes based on vertical-axis components applicable to all attributes data. For example, a configuration may be used in which, for some attributes data, retrieval conditions can be created based only on the processes based on horizontal-axis components. In this case, it is preferable to create relationship data indicating the applicable processes from among the processes based on horizontal-axis components and the processes based on vertical-axis components for each item of attributes data. In the following description, a data-type memory 7 that stores such relationship data is provided.

Figure 11:
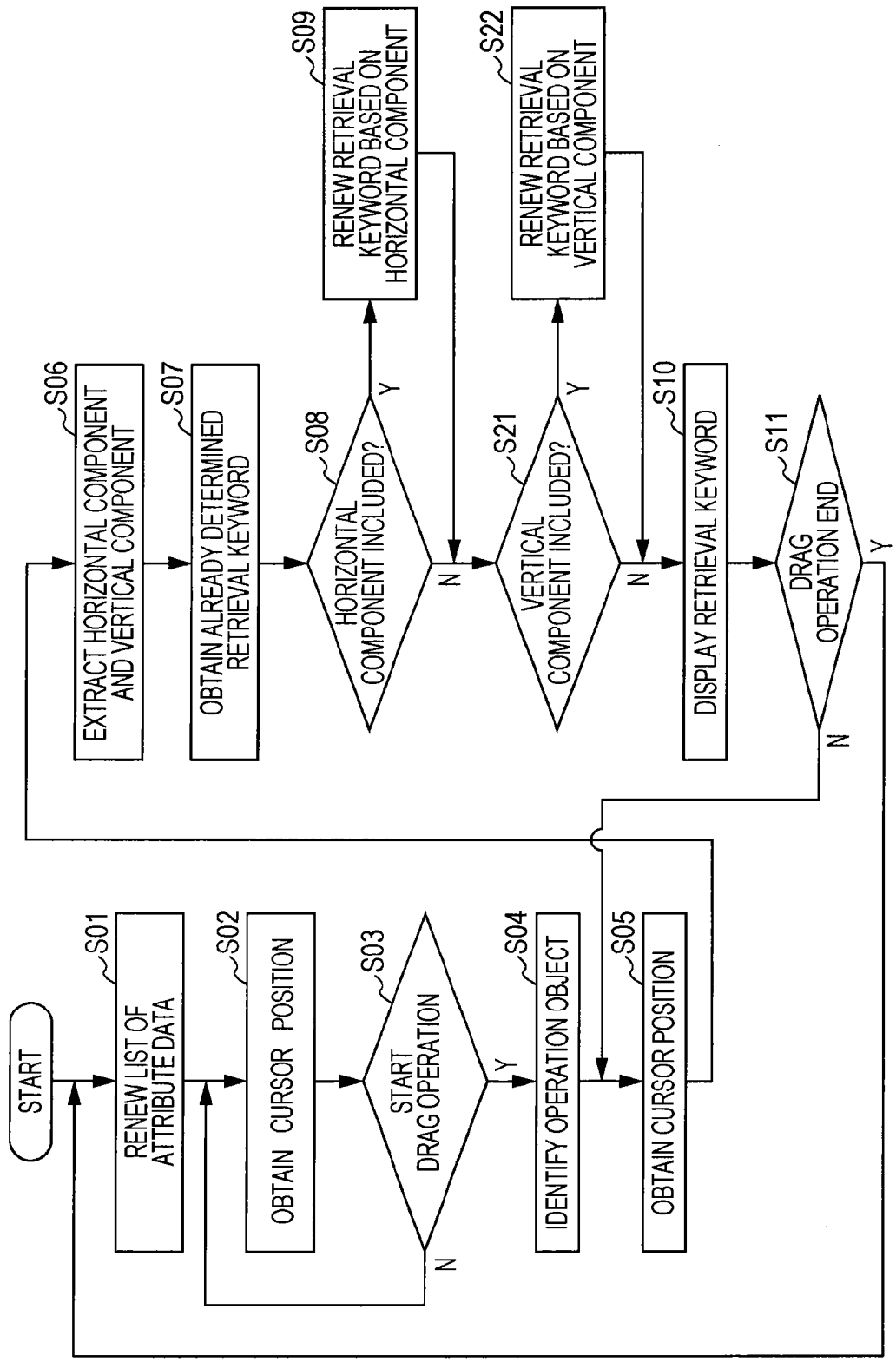
FIG. 11 is a flowchart of a medical image processing apparatus according to the second embodiment.

Next, a series of operations performed during a drag operation will be described with reference to FIG. 11, with a focus on parts different from the medical image processing apparatus according to the first embodiment. FIG. 11 is a flowchart showing operations performed during a drag operation of the medical image processing apparatus.

The processes from steps S01 through S07 are the same as those for the medical image processing apparatus according to the first embodiment. Therefore, detailed descriptions will be omitted. During the course of these processes, the keyword-generating part 6 receives the vertical-axis components and horizontal-axis components of the vector calculated based on the position information of the start point and the position information of the cursor 41*b* from the operation-details analyzer 33. Moreover, the keyword-generating part 6 confirms whether or not retrieval conditions have already been created for the attributes of the operation object data. If retrieval conditions have already been created, the keyword-generating part 6 generates partial data that acts as the foundation based on the retrieval conditions.
(Step S08)

The keyword-generating part 6 confirms whether or not horizontal-axis components are included in the vector calculated by the operation-details analyzer 33.
(Step S09)

If horizontal-axis components are included in the vector (Step S08: Y), the keyword-generating part 6 creates retrieval conditions based on the horizontal-axis components and the operation object data. In this case, the keyword-generating part 6 creates different retrieval conditions depending on whether the direction of the horizontal-axis components is left or right. If the direction is left, the keyword-generating part 6 creates suitable conditions based on information indicating the amount of movement in the leftward direction that is included in the horizontal-axis components. Moreover, if the direction is right, the keyword-generating part 6 creates unsuitable conditions based on information indicating the amount of movement in the rightward direction that is included in the horizontal-axis components. If no horizontal-axis components are included in the vector (Step S08: N), these processes are not performed.
(Step S21)

Moreover, the keyword-generating part 6 confirms whether or not vertical-axis components are included in the vector calculated by the operation-details analyzer 33.
(Step S22)

If vertical-axis components are included in the vector (Step S21: Y), the keyword-generating part 6 changes the tail data of the retrieval conditions to create new retrieval conditions based on both information indicating the direction along the vertical axis and information indicating the amount of movement along the vertical axis. If no vertical-axis components are included in the vector (Step S21: N), these processes are not performed.
(Step S10)

When the retrieval conditions are created, the keyword-generating part 6 outputs the retrieval conditions to the data-list-display controller 31, allowing the data-list-display controller 31 to display the retrieval conditions on the operation screen 41*a*.
(Step S11)

If the drag operation is continuing (Step S11: N), the cursor controller 32 continues monitoring the position of the cursor 41*b*. When the drag operation ends (Step S11: Y), the operation-details analyzer 33 notifies the keyword-generating part 6 of the end of the drag operation. The keyword-generating part 6 receives the notification of the end of the drag operation and outputs the created retrieval conditions to the retrieval part 2. The retrieval part 2 searches the data memory 1 based on the retrieval conditions. The data-list-display controller 31 receives the retrieval results and updates the data list. As a result, upon receiving the drag operation performed by the operator, the rows displayed in the data list are narrowed down in real time based on the retrieval conditions. Subsequently, as long as operations by the operator continue, the medical image processing apparatus repeatedly executes the above processes. Upon detecting the end of operations, the medical image processing apparatus ends the above processes by stopping the operations of each configuration.

Furthermore, as with the medical image processing apparatus according to the first embodiment, instead of operations to monitor the position of the cursor and acquire position information, operations to receive operations of the cursor and acquire the position information of the start point may be applied.

As described above, according to the medical image processing apparatus of the second embodiment, based on drag operations in the vertical-axis direction, it becomes possible to create retrieval conditions different from those created through operations in the horizontal-axis direction and to update the data list.

(Third Embodiment)

Figure 12:
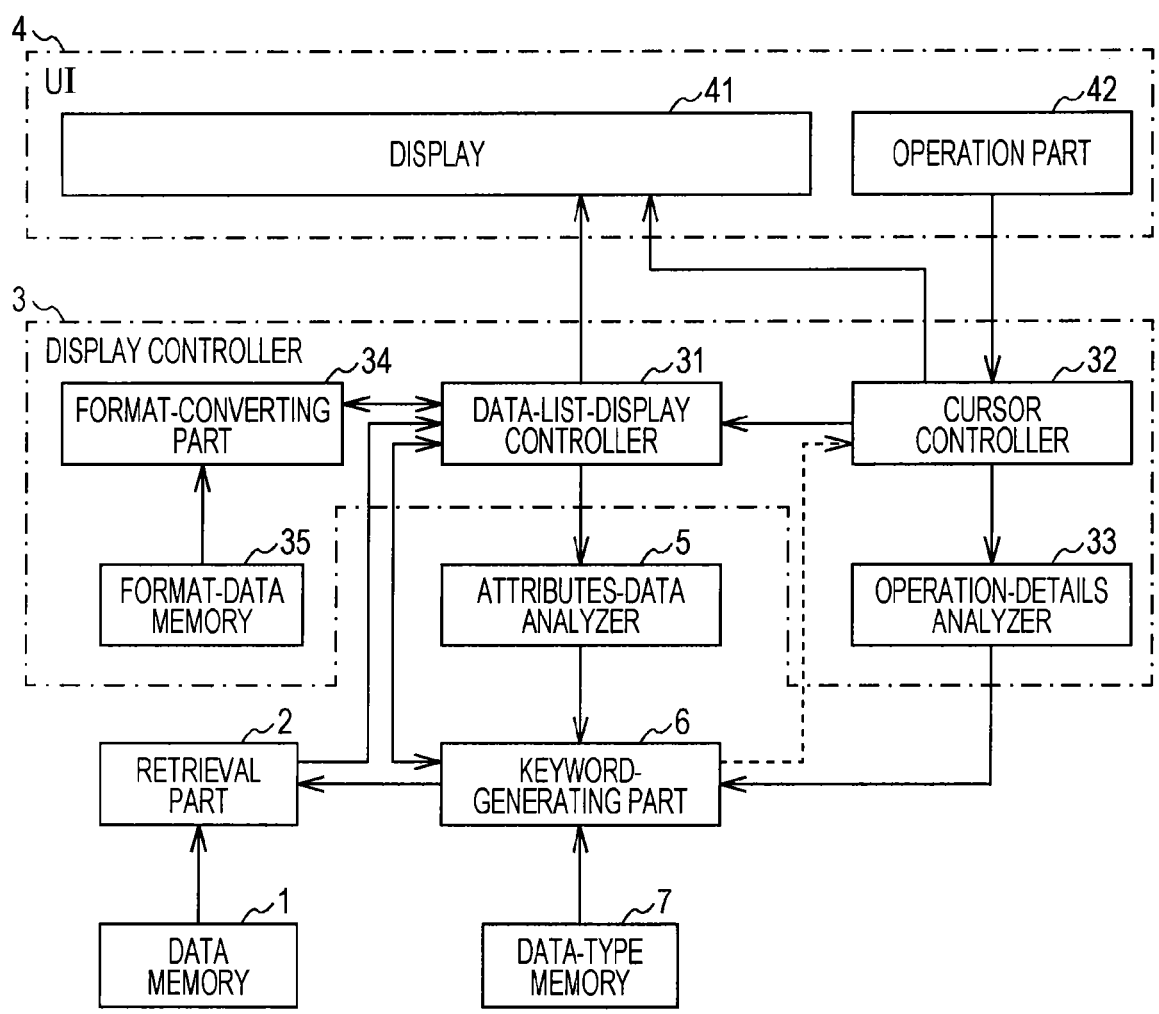
FIG. 12 is a block diagram of a medical image processing apparatus according to the third embodiment.

Within the attributes data correlated with the medical data, there are attributes data that may be expressed in different formats. For example, the attributes data indicating the date "Feb. 15, 2010" may be expressed as "Feb. 15, 2010," "Feb. 15, 2010," or "Feb. 15, 2010." The medical image processing apparatus according to the third embodiment converts such attributes data that may be expressed in different formats into a predetermined format and causes them to be displayed in a data list. The following is a description of the configuration of the medical image processing apparatus according to the third embodiment with reference to FIG. 12, with a focus on configurations different from those of the medical image processing apparatus according to the first embodiment. FIG. 12 is a block diagram of the medical image processing apparatus according to the third embodiment.

The display controller 3 according to the present embodiment further includes a format-converting part 34 and a format-data memory 35. The following is a description of the operations of the format-converting part 34, the data-list-display controller 31, and the format-data memory 35.

(Format-Data Memory 35)

In the format-data memory 35, for attributes data that may be expressed in different formats, the formats of those attributes data are correlated and stored. For example, in the case of attributes data indicating the date, a format for the expression "2/15/2010", a format for the expression "Feb. 15, 2010", and a format for the expression "2010/02/15" are correlated and stored.

(Data-List-Display Controller 31)

If attributes data that may be expressed in different formats are included in the data list, the data-list-display controller 31 according to the present embodiment causes the format-converting part 34 (described later) to convert the attributes data. In this case, the data-list-display controller 31 is preferably configured to discriminate whether the attributes data can be expressed or not in different formats based on, for example, the data type of the attributes data. Moreover, the data-list-display controller 31 may discriminate whether the attributes data can be expressed or not in different formats by referring to the format-data memory 35.

(Format-Converting Part 34)

Upon receiving attributes data to be converted from the data-list-display controller 31, the format-converting part 34 searches the format-data memory 35 and extracts a list of the formats of the attributes data. Based on the extracted list of formats, the format-converting part 34 identifies the current format of the attributes data. The format-converting part 34 divides the attributes data into units of data based on the identified current format, and converts the data to a new format by reconfiguring the data into a predetermined format. The format-converting part 34 outputs the attributes data of the new format to the data-list-display controller 31, allowing the data-list-display controller 31 to cause the attributes data to be displayed in the data list based on the predetermined format.

As described above, the medical image processing apparatus of the third embodiment allows attributes data that may be expressed in different formats to be displayed according to predetermined formats. As a result, the user becomes able to designate retrieval conditions through common operations regardless of the format of the attributes data.

(Fourth embodiment)

The medical image processing apparatus according to the fourth embodiment combines two or more items of attributes data from among the attributes data stored in the data memory 1 and displays them in a single field in the data list. Specifically, the medical image processing apparatus combines, for example, the attributes data for "Last name" with the attributes data for "First name" and displays them in the column for "Name." When a drag operation is performed on the "Name" field, the medical image processing apparatus identifies whether the operation object data are the "Last name" or the "First name" and creates retrieval conditions. The following is a description of the configuration of medical image processing apparatus according to the present embodiment, with a focus on configurations of the data-list-display controller 31 different from those of the medical image processing apparatus according to the first embodiment.

(Data-List-Display Controller 31)

Figure 13:
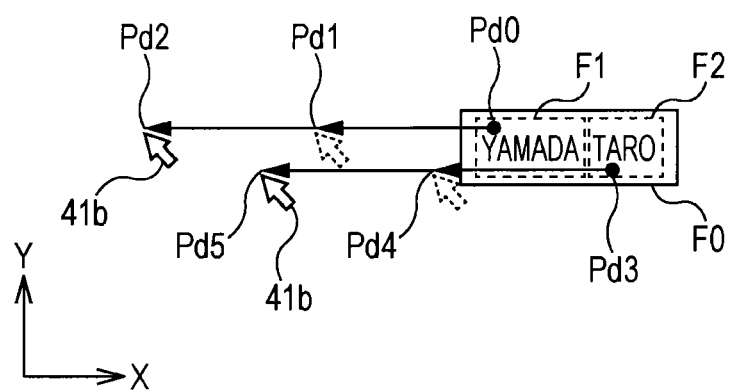
FIG. 13 is a diagram for describing operations during a drag operation when multiple items of attributes data are included in a single item.

The data-list-display controller 31 according to the fourth embodiment causes predetermined two or more items of attributes data to be displayed in a single column. In this case, the data-list-display controller 31 divides the field F0 corresponding to "Name" into a region F1 and a region F2 as shown in FIG. 13, for example. In this case, the data-list-display controller 31 associates the attributes data for "Last name" with the region F1 and the attributes data for "First name" with the region F2.

Next, operations performed when such a field in which two or more items of attributes data are associated is subject to a drag operation will be described, using the field F0 associated with "Name" as an example. The data-list-display controller 31 receives position information corresponding to the start point of the drag operation from the cursor controller 32. In this case, if the position information of the start point is included in the region F1, the data-list-display controller 31 sets the attributes data for "Last name" as the operation object data.

If, for example, a drag operation is performed from the start point of the position Pd0 to the position Pd1 or Pd2 as shown in FIG. 13, the data-list-display controller 31 sets the "Last name" attributes data "Yamada" as the operation object data. Moreover, if the position information of the start point is included in the region F2, the data-list-display controller 31 identifies the attributes data for "First name" as the operation object data. If, for example, a drag operation is performed from the start point of the position Pd3 to the position Pd4 or Pd5 as shown in FIG. 13, the data-list-display controller 31 identifies the "First name" attributes data "Taro" as the operation object data.

Subsequently, as with the medical image processing apparatus according to the first embodiment or the second embodiment, retrieval conditions are created based on the identified operation object data and operation information of the drag operation. Furthermore, a single item of attributes data may be divided into multiple items of data, and a region may be associated with each item of data. For example, the attributes data for "Examination date" may be divided into the data "Year", "Month", and "Day", and a region may be assigned to each. In this case, each of the "Year", "Month", and "Day" is preferably separately defined as an operation object. Moreover, the processes for dividing the "Examination date" into the data "Year", "Month", and "Day" may be executed by the format-converting part 34, for example.

As described above, the medical image processing apparatus according to the fourth embodiment allows multiple items of attributes data to be displayed in a single field according to a desired format. Moreover, this case allows the medical image processing apparatus to distinguishably identify a plurality of the multiple items of attributes data displayed in the single field as an operation object and to create retrieval conditions.

(Fifth Embodiment)

Figure 14:
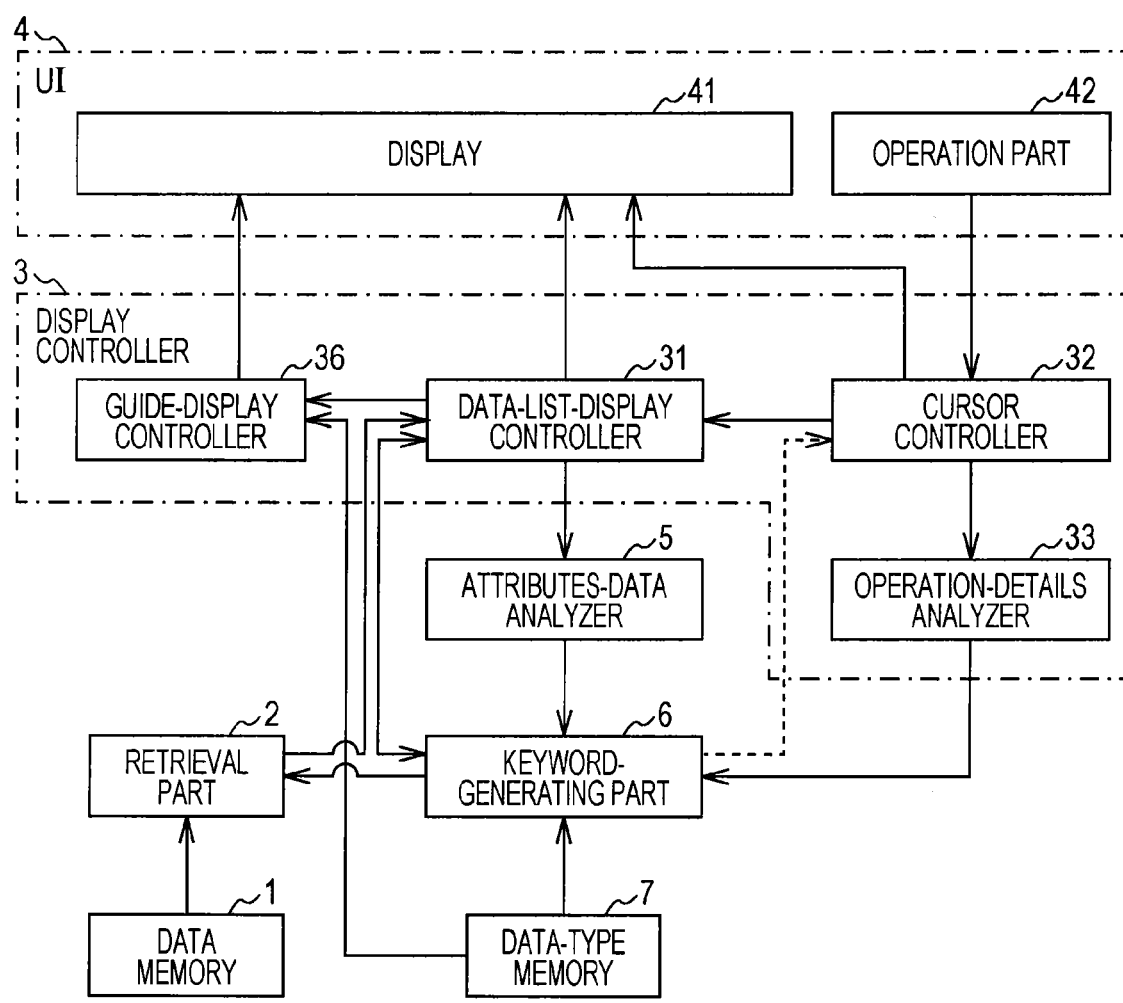
FIG. 14 is a block diagram of a medical image processing apparatus according to the fifth embodiment.

The fact that it is possible to associate either or both of processes based on horizontal-axis components and processes based on vertical-axis components with each item of attributes data has been described in the second embodiment. The medical image processing apparatus according to the fifth embodiment, if no cursor operation is performed over a predetermined and prescribed time period, is intended to cause the display 41 to display a guide for presenting processes applicable to the attributes data corresponding to the position information of the cursor 41b. The following is a description of configurations of the medical image processing apparatus according to the fifth embodiment with reference to FIG. 14, with an emphasis on configurations different from those of the medical image processing apparatus according to the second embodiment. FIG. 14 is a block diagram of the medical image processing apparatus according to the fifth embodiment.

The display controller 3 according to the present embodiment also includes a guide-display controller 36. The following description focuses on the operations of the cursor controller 32, the data-list-display controller 31, and the guide-display controller 36.

(Cursor Controller 32, Data-List-Display Controller 31)

If the position of the cursor 41 has not been changed for a predetermined time period, the cursor controller 32 provides notification to the data-list-display controller 31 of the fact that the cursor 41b has not been operated, together with the position information of the cursor 41b. Upon receiving this notification, the data-list-display controller 31 identifies the attributes data corresponding to the position information of the cursor 41b. The data-list-display controller 31 provides notification to the guide-display controller 36 defining the identified attributes data as the display object for the guide.

(Guide-Display Controller 36)

Figure 15:
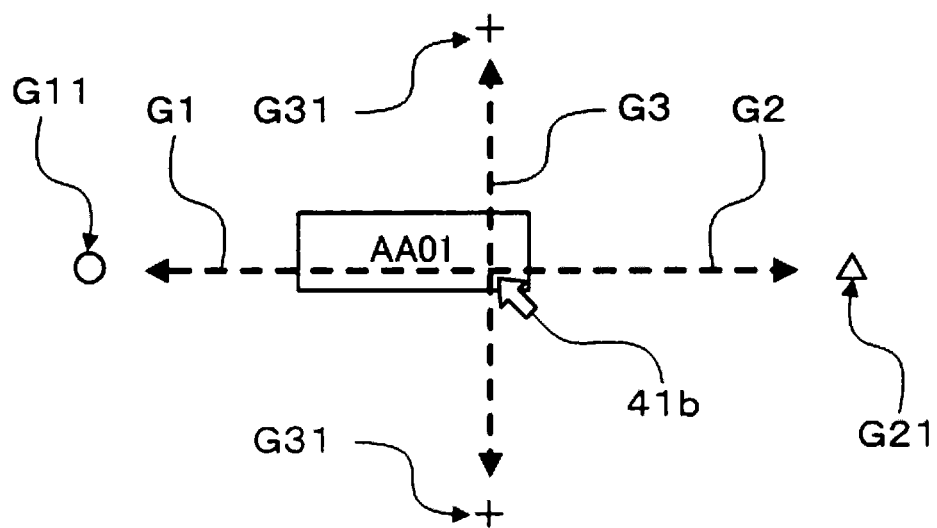
FIG. 15 is an example of a guide display.
Figure 16:
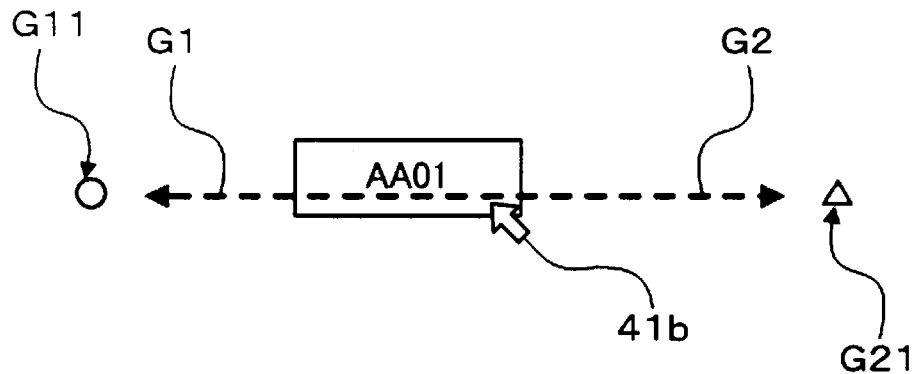
FIG. 16 is an example of a guide display.

The guide-display controller 36 extracts relationship data corresponding to the attributes data from the data-type memory 7. Based on the extracted relationship data, the guide-display controller 36 creates a guide presenting processes that are applicable to the attributes data. This guide is displayed for presenting to the operator the directions of operations applicable to the attributes data. On this guide, arrows pointing in the directions of operations applicable to the attributes data are displayed, for example. As a result, the operator becomes able to confirm the operations applicable to the attributes data. For example, FIG. 15 and FIG. 16 show examples of this guide display.

First, a case will be described in which both processes based on horizontal-axis components and processes based on vertical-axis components are applicable to the attributes data. As shown in FIG. 15, the guide-display controller 36 creates a guide including the arrows G1 and G2 indicating directions along the horizontal axis as well as the arrow G3 along the vertical axis. In this case, icons for identifying the processes corresponding to the operations in each direction may be displayed. For example, as shown in FIG. 15, it is preferable to associate the leftward arrow G1 with an icon G11 indicating the creation of suitable conditions to be displayed. Moreover, the rightward arrow G2 is associated with an icon G21 indicating the creation of unsuitable conditions to be displayed in contrast to the leftward icon G11. Moreover, for the upward and downward arrow G3, in contrast to operations in the horizontal-axis directions, an icon G31 indicating processes based on vertical-axis components is displayed.

Next, a case will be described in which only processes based on horizontal-axis components are applicable to the attributes data. In this case, as shown in FIG. 16, the guide-display controller 36 creates a guide that includes only the arrows G1 and G2 indicating directions along the horizontal axis. The guide-display controller 36 causes the display 41 to display the created guide. Moreover, as with the example of FIG. 15, icons for identifying the processes corresponding to the operations in each direction may be displayed. For example, as shown in FIG. 16, for the leftward arrow G1, it is preferable to display the icon G11 indicating the creation of suitable conditions. Moreover, for the rightward arrow G2, the icon G21 indicating the creation of unsuitable conditions is associated and displayed.

Figure 17:
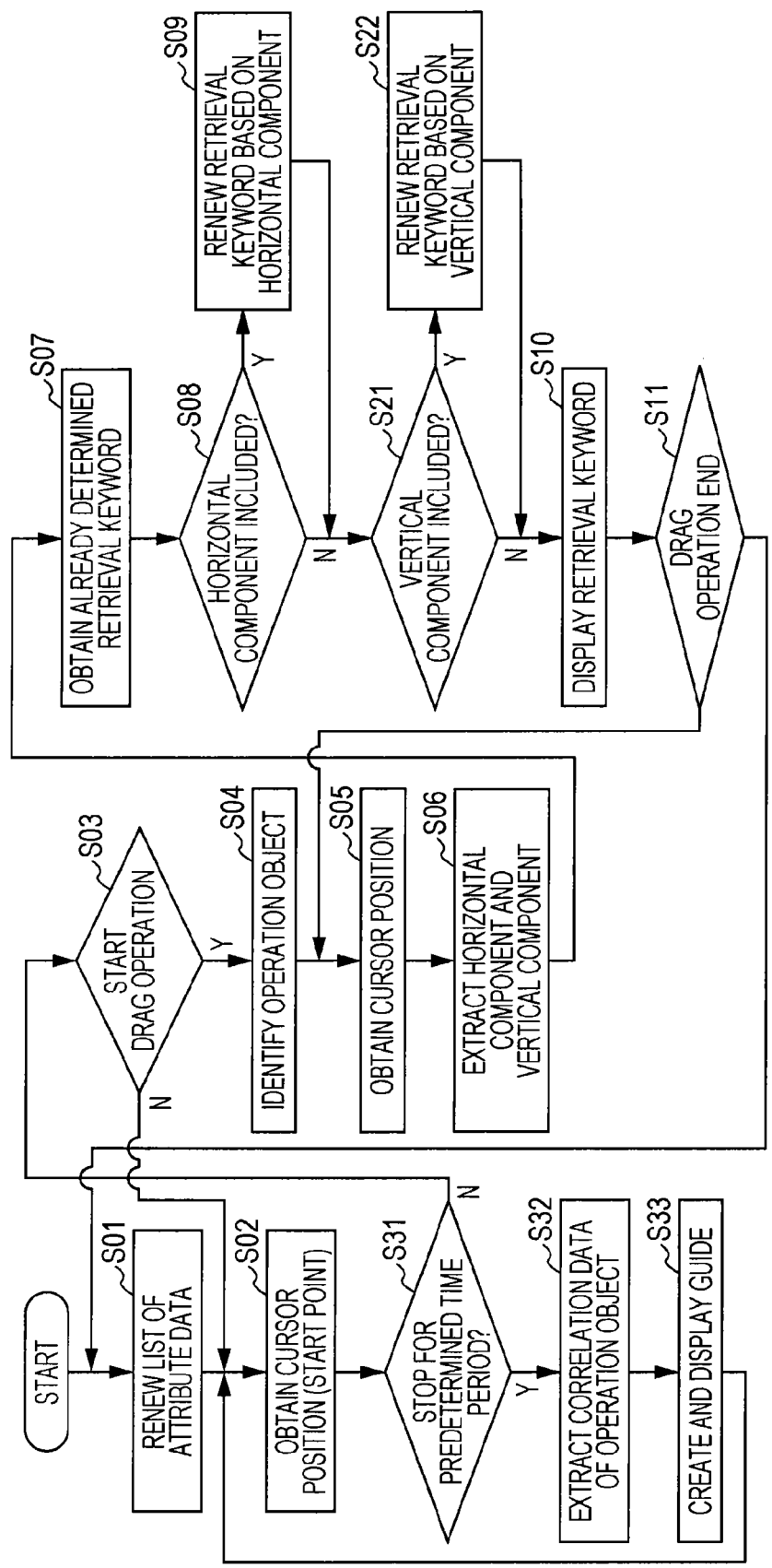
FIG. 17 is a flowchart of a medical image processing apparatus according to the fifth embodiment.

Next, a series of operations performed by the medical image processing apparatus according to the fifth embodiment will be described with reference to FIG. 17, with a focus on processes different from those of the second embodiment. FIG. 17 is a flowchart of processes related to cursor operations of the medical image processing apparatus.

(Step S01)

When the operator executes an operation related to the retrieval of medical data, upon receiving this operation, the retrieval part 2 first searches the data memory 1 and reads out a list of attributes data. The list of attributes data that is read out by the retrieval part 2 is formed in a tabular form and displayed on the operation screen 41a by the data-list-display controller 31.

(Step S02)

When the operation screen 41a is displayed, the cursor controller 32 sequentially monitors the position of the cursor 41b and acquires the position information of the cursor 41b.

(Step S31)

If the position of the cursor 41b is not changed for a predetermined time period (Step S31: Y), the cursor controller 32 provides notification to the data-list-display controller 31 of the fact that the cursor 41b has not been operated, together with the position information of the cursor 41b. Upon receiving this notification, the data-list-display controller 31 identifies the attributes data corresponding to the position information of the cursor 41b. The data-list-display controller 31 provides notification to the guide-display controller 36 defining the identified attributes data as the display object for the guide.

(Step S32)

The guide-display controller 36 extracts relationship data corresponding to the attributes data of the notification from the data-list-display controller 31 from the data-type memory 7.

(Step S33)

Based on the extracted relationship data, the guide-display controller 36 creates a guide that presents processes applicable to the attributes data. The guide-display controller 36 causes the display 41 to display the created guide.

If a cursor operation is detected (Step S31: N), the cursor controller 32 executes the processes of step S03 onward. The processes of step S03 onward are the same as those of the medical image processing apparatus according to the second embodiment, thus detailed descriptions is omitted.

As with the medical image processing apparatus according to the first embodiment, instead of operations to sequentially monitor the position of the cursor and acquire position information, operations to receive operations of the cursor and acquire position information may be applied. In this case, the operations related to steps 02 and S31-S33, for example, may be replaced by processes for acquiring the position information of the cursor when the cursor stops for a prescribed time period. Moreover, for the steps S02 and S03, processes for acquiring the position information of the start point when a drag operation starts may be applied instead.

As described above, according to the medical image processing apparatus of the fifth embodiment, it becomes possible to present the operator with processes applicable to the attributes data.

(Sixth embodiment)

Figure 18:
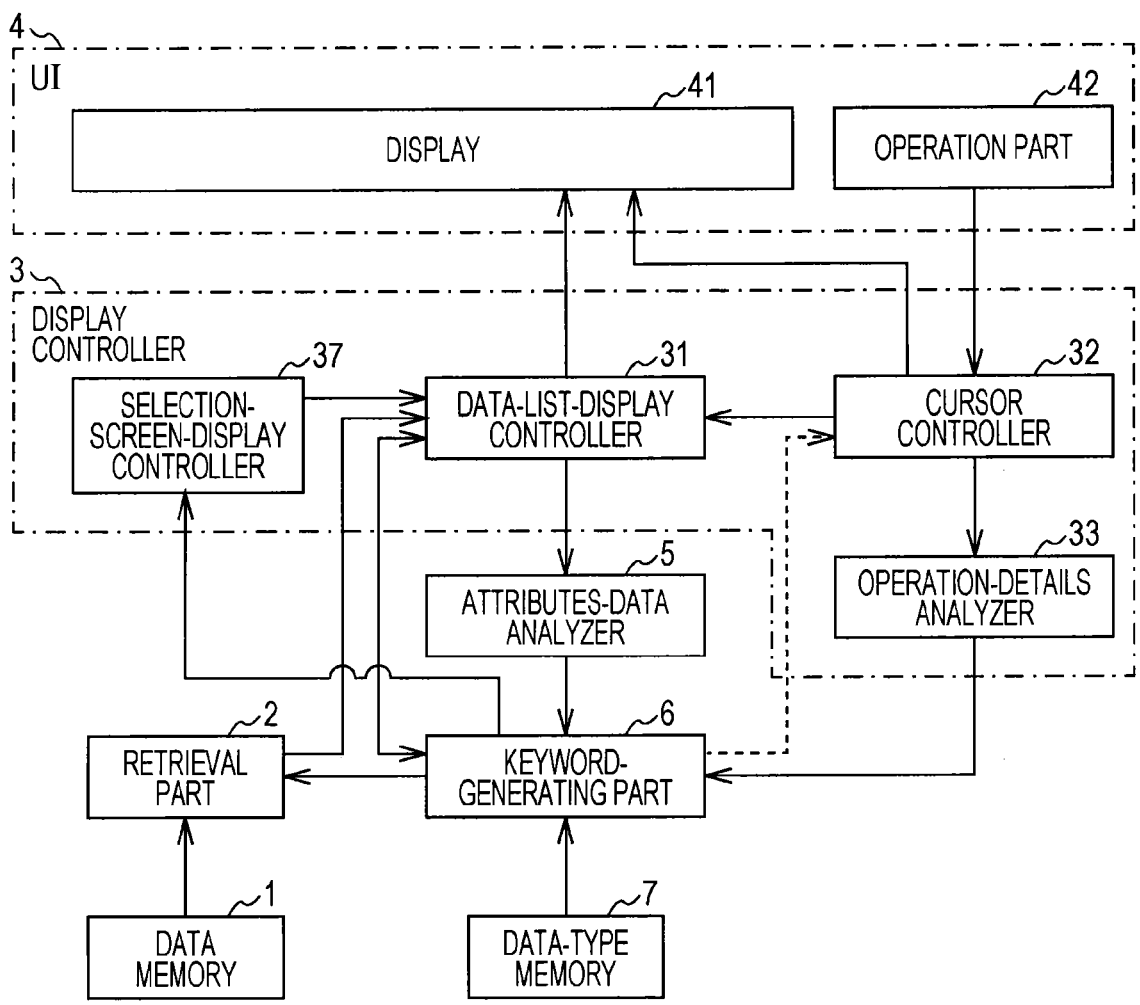
FIG. 18 is a block diagram of a medical image processing apparatus according to the sixth embodiment.

The attributes data correlated with the medical data include attributes data to which only one of predetermined sets of data (hereinafter also referred to as "data with selection candidates") is set. For example, for attributes data indicating a day of the week, the selection candidates are "Sunday" to "Saturday," and only one of these selection criteria is set. If a drag operation is performed with such an item of attributes data as the operation object, the medical image processing apparatus according to the sixth embodiment displays a screen displaying a list of selection candidates (hereinafter also referred to as a "selection screen"). As a result, the operator may select a selection candidate displayed on the selection screen to cause the medical image processing apparatus to create retrieval conditions. The following is a description of configurations of the medical image processing apparatus according to the sixth embodiment with reference to FIG. 18. FIG. 18 is a block diagram of the medical image processing apparatus according to the sixth embodiment.

The display controller 3 according to the present embodiment also includes a selection-screen display controller 37. The following description is divided between the "displaying of the selection screen" and the "creation of retrieval conditions" to describe configurations related to each operation, with a focus on parts different from the medical image processing apparatus according to the second embodiment.

(Displaying of the Selection Screen)

First, configurations related to the displaying of a selection screen will be described. When displaying an operation screen, the keyword-generating part 6 and the selection-screen display controller 37 operate. The following is a description of the operations of each configuration.

(Keyword-Generating Part 6)

The keyword-generating part 6 according to the present embodiment first identifies whether or not the operation object data are data with selection candidates. In this case, the keyword-generating part 6 is preferably configured to identify whether or not the data have selection candidates based on the data type of the operation object data. Moreover, an indication of whether or not the data have selection candidates may be included in the relationship data and stored in the data-type memory 7 in advance.

If the operation object data are data with selection candidates, the keyword-generating part 6 identifies the selection candidates of the operation object data. In this case, it is preferable to create information for identifying selection candidates that correlates the attributes of the data having selection candidates with the selection candidates. For example, in the case of attributes data indicating the days of the week, it is preferable to correlate the attribute "Day of the week" with the selection candidates "Sunday" to "Saturday" and create information for identifying the selection candidates. This information for identifying the selection candidates may be stored in advance in the keyword-generating part 6, or may be included in the relationship data and stored in the data-type memory 7. The keyword-generating part 6 outputs the identified selection candidates to the selection-screen display controller 37.

(Selection-Screen Display Controller 37)

Figure 19:
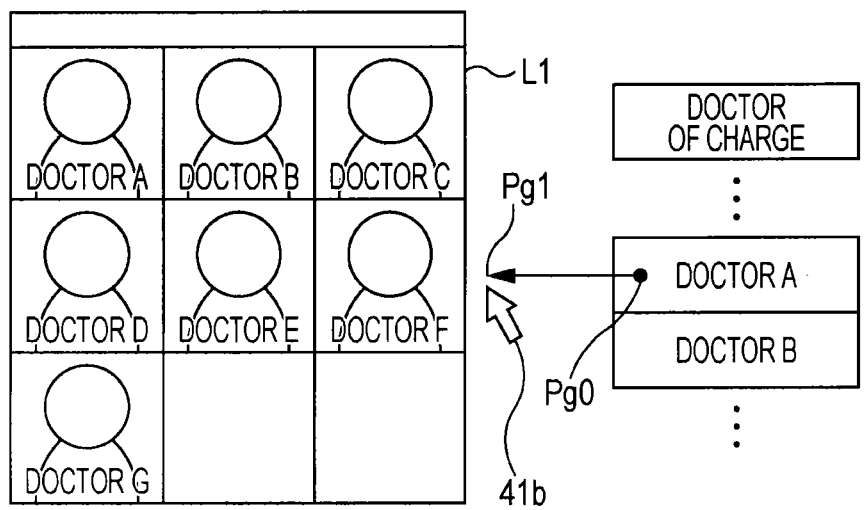
FIG. 19 is an example of a selection screen.

The selection-screen display controller 37 creates a selection screen in which the selection candidates received from the keyword-generating part 6 are displayed in a manner in which they may be selected by the cursor 41b. This description uses the example of attributes data for the attribute "Physician in charge", which includes "Physician A" to "Physician G" for the selection candidates. In this case, as shown in FIG. 19, the selection-screen display controller 37 creates a selection screen L1 in which "Physician A" to "Physician G" are displayed. In this case, image data of headshots of the physicians, etc. or icons, for example, may be displayed as well.

Figure 20:
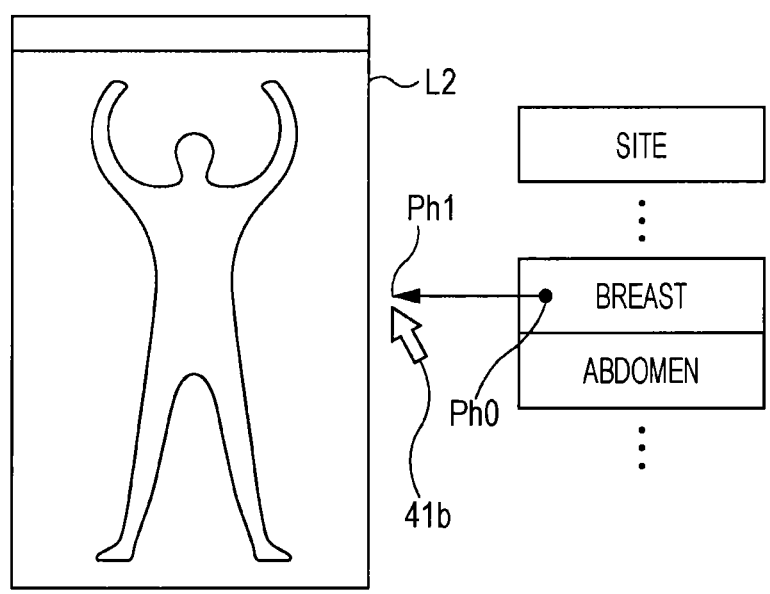

Moreover, for the attributes data for the attribute "Site," one item of information indicating a site, such as "Chest" or "Abdomen," is set. In other words, the selection candidates corresponding to the attribute "Site" are configured by information indicating sites, such as "Chest" and "Abdomen." In the case of such attributes data for the attribute "Site," as shown in FIG. 20, a selection screen L2 that displays an image representing the body may be created. In this case, the selection-screen display controller 37 may cause the selection candidates "Chest" and "Abdomen," etc. as the attributes data indicating the "Site" to be displayed to be associated with the regions indicating each site in the image representing the body.

The selection-screen display controller 37 outputs the created selection screen to the data-list-display controller 31. The data-list-display controller 31 causes the display 41 to display the selection candidates on the selection screen to be associated with the position information on the display 41.

(Creations of Retrieval Conditions)

Next, configurations related to the creation of retrieval conditions will be described. When any one of the selection candidates displayed on the selection screen is clicked, the cursor controller 32, the data-list-display controller 31, and the keyword-generating part 6 operate. As a result of a series of processes performed by these configurations, retrieval conditions for retrieving medical data are created. The following is a description of operations of these configurations related to the creation of retrieval conditions.

(Cursor Controller 32)

The cursor controller 32 receives a click operation performed by the operator and outputs the position information of the cursor 41b to the data-list-display controller 31.

(Data-List-Display Controller 31)

The data-list-display controller 31 identifies the selection candidates corresponding to the position information. The data-list-display controller outputs the identified selection candidates and the attributes data corresponding to the selection screen to the keyword-generating part 6.

(Keyword-Generating Part 6)

Based on the attributes data and the selection candidates, the keyword-generating part 6 creates retrieval conditions for updating the data list. In this case, the keyword-generating part 6 may switch between created retrieval conditions depending on the direction of the drag operation when the selection screen is displayed. For example, if the selection screen is displayed as a result of a drag operation in the leftward direction, the keyword-generating part 6 is configured to create suitable conditions. Moreover, if the selection screen is displayed as a result of a drag operation in the rightward direction, the keyword-generating part 6 is configured to create unsuitable conditions.

The keyword-generating part 6 outputs the created retrieval conditions to the retrieval part 2. The retrieval part 2 receives the retrieval conditions and searches the data memory 1 based on the retrieval conditions. The data-list-display controller 31 receives the retrieval results and updates the data list. As a result, in accordance with drag operations performed by the operator, the rows displayed in the data list are narrowed down in real time based on the retrieval conditions.

Figure 21:
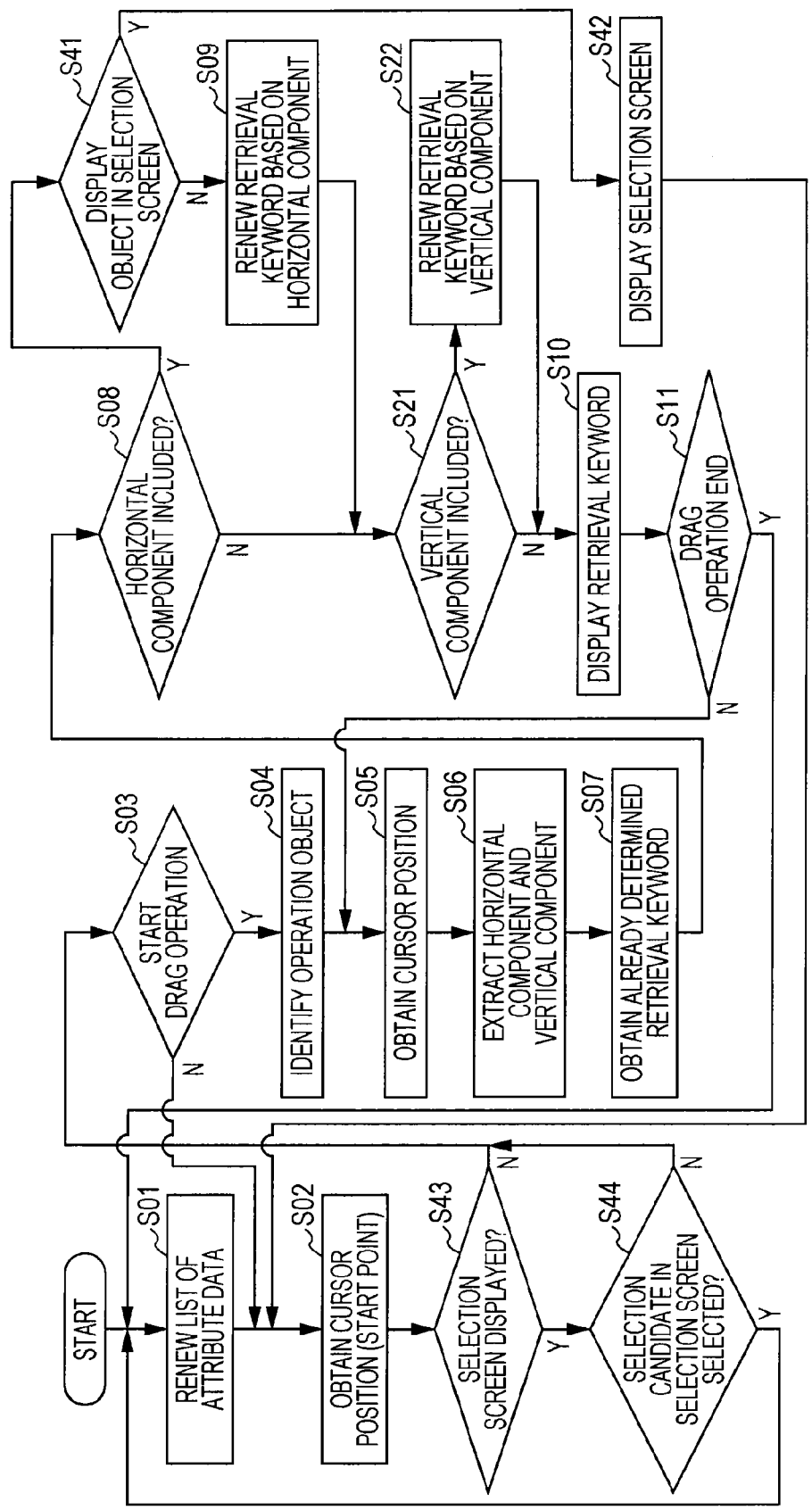
FIG. 21 is a flowchart of a medical image processing apparatus according to the sixth embodiment.

Next, a series of operations of the medical image processing apparatus according to the sixth embodiment will be described with reference to FIG. 21, starting from a state in which no selection screen is displayed. FIG. 21 is a flowchart of operations performed during a drag operation of the medical image processing apparatus.

(Step S01)

When the operator executes an operation related to the retrieval of medical data, the retrieval part that receives this operation searches the data memory 1 and reads out a list of attributes data. The data-list-display controller 31 forms the list of attributes data in a tabular form and causes it to be displayed on the operation screen 41a. At this stage, no selection screen is displayed on the display 41.

(Steps S02, S43)

When the operation screen 41a is displayed, the cursor controller 32 sequentially monitors the position of the cursor 41b and acquires the position information of the cursor 41b (Step S02). At this point, no selection screen is displayed (Step S42: N). Therefore, the operations proceed to processes related to step S03.
(Steps S03-S07)
In the following, the medical image processing apparatus according to the present embodiment executes processes related to the steps S03-S07. Furthermore, the processes related to the steps S03-S07 are the same as those of the medical image processing apparatus according to the second embodiment, and therefore, details descriptions will be omitted. Through the course of these processes, the keyword-generating part 6 receives the vertical-axis components and horizontal-axis components of the vector calculated based on the position information of the start point and the position information of the cursor 41*b* from the operation-details analyzer 33. Moreover, the keyword-generating part 6 confirms whether or not retrieval conditions have already been created for the attributes of the operation object data. If retrieval conditions have already been created, partial data that act as the foundation are generated based on the retrieval conditions.
(Step S08)
The keyword-generating part 6 confirms whether or not horizontal-axis components are included in the vector calculated by the operation-details analyzer 33.
(Step S41)
If horizontal-axis components are included in the vector (Step S08: Y), the keyword-generating part 6 identifies whether or not the operation object data are data with selection candidates.
(Step S42)
If the operation object data are data with selection candidates (Step S41: Y), the keyword-generating part 6 identifies the selection candidates of the operation object data. The keyword-generating part 6 outputs the identified selection candidates to the selection-screen display controller 37. The selection-screen display controller 37 creates a selection screen in which the selection candidates received from the keyword-generating part 6 are displayed in a manner in which they may be selected by the cursor 41*b*. The selection-screen display controller 37 outputs the created selection screen to the data-list-display controller 31. The data-list-display controller 31 causes the display 41 to display the selection candidates on the selection screen to be associated with position information on the display 41. Then, once the drag operation ends, the operations proceed to processes related to step S02.
(Steps S09, S21, S22, S10, and S11)
If the operation object data are not data with selection candidates (Step S41: N), the processes related to step S09, step S21, step S22, step S10, and step S11 are executed. These processes are the same as those of the medical image processing apparatus according to the second embodiment, and therefore, detailed descriptions will be omitted.
Next, operations performed when a selection screen is being displayed as a result of the processes related to step S42 will be described, with a focus on operations performed when a selection candidate on the selection screen is clicked.
(Steps S02, S43)
The cursor controller 32 continues monitoring the cursor 41*b* and acquires the position information of the cursor 41*b*. When a click operation is performed by the operator, the cursor controller 32 outputs the position information of the cursor 41*b* to the data-list-display controller 31 (Step S02). At this stage, the selection screen is already being displayed on the display 41 as a result of the processes of step S42 (Step S42: Y). Therefore, operations proceed to the processes related to step S44.

Figure 22:
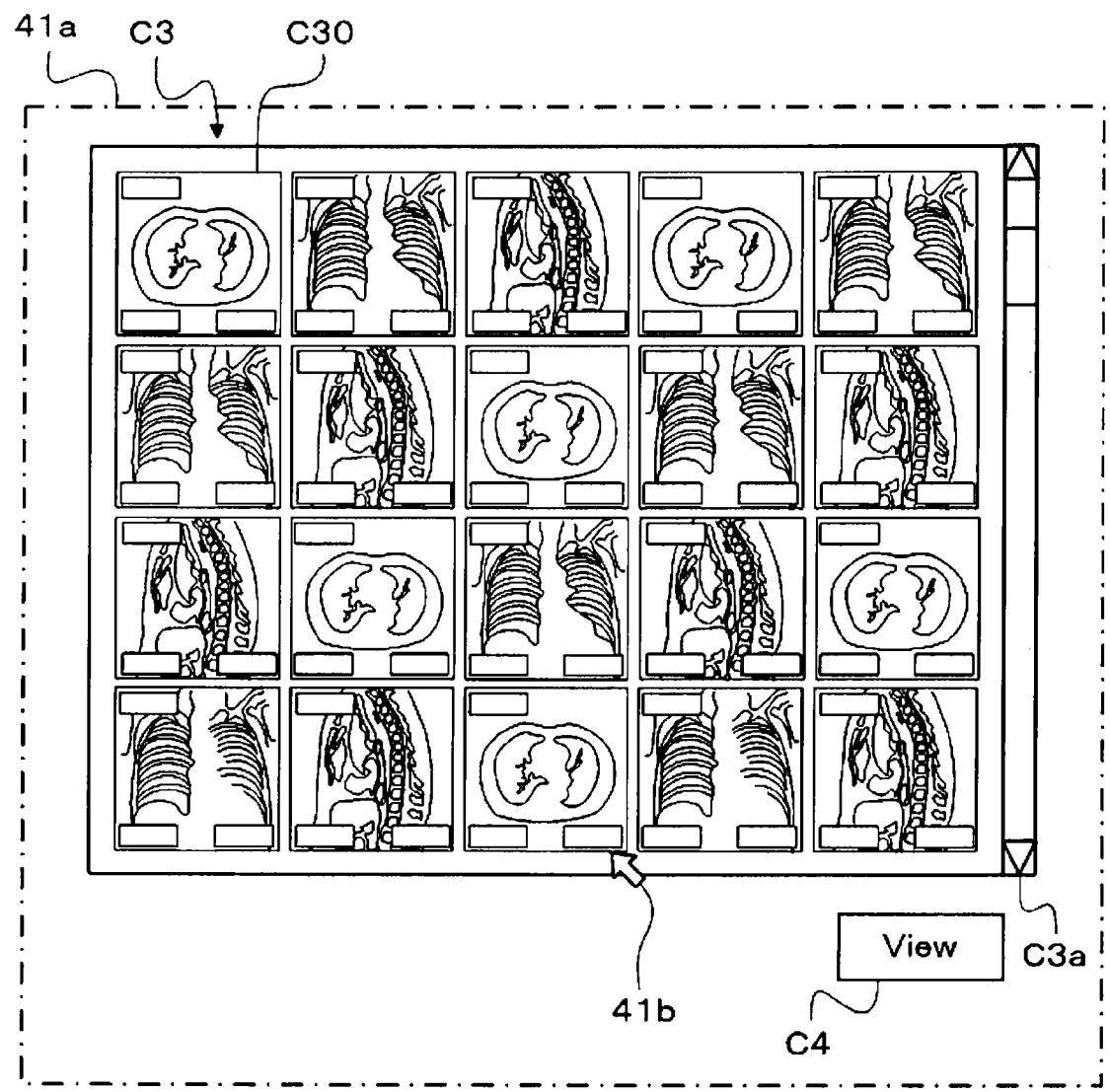
FIG. 22 is an example of an operation screen of a medical image processing apparatus according to a variation.
Figure 23:
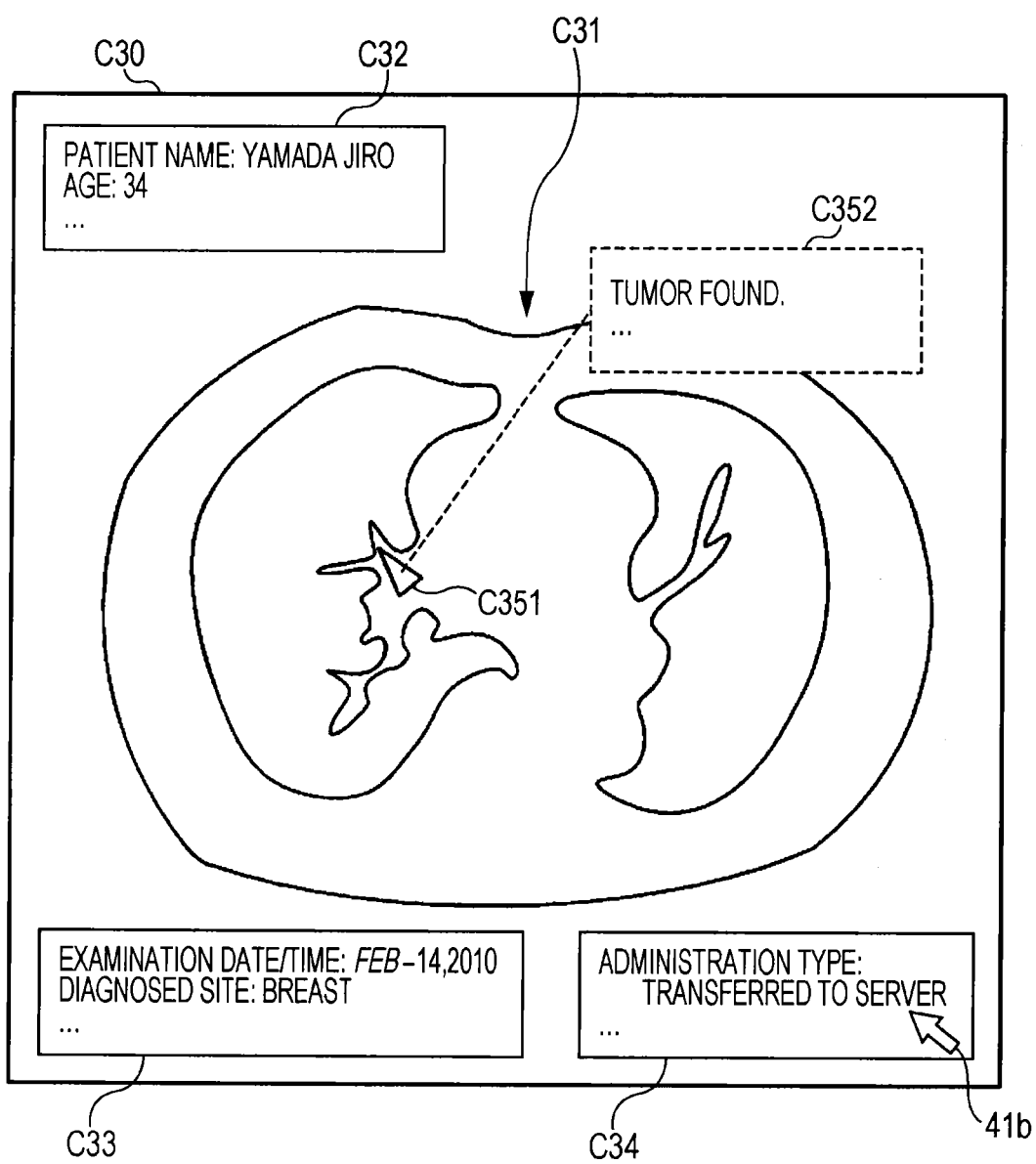
FIG. 23 is an example of an operation screen of a medical image processing apparatus according to a variation.
Figure 24:
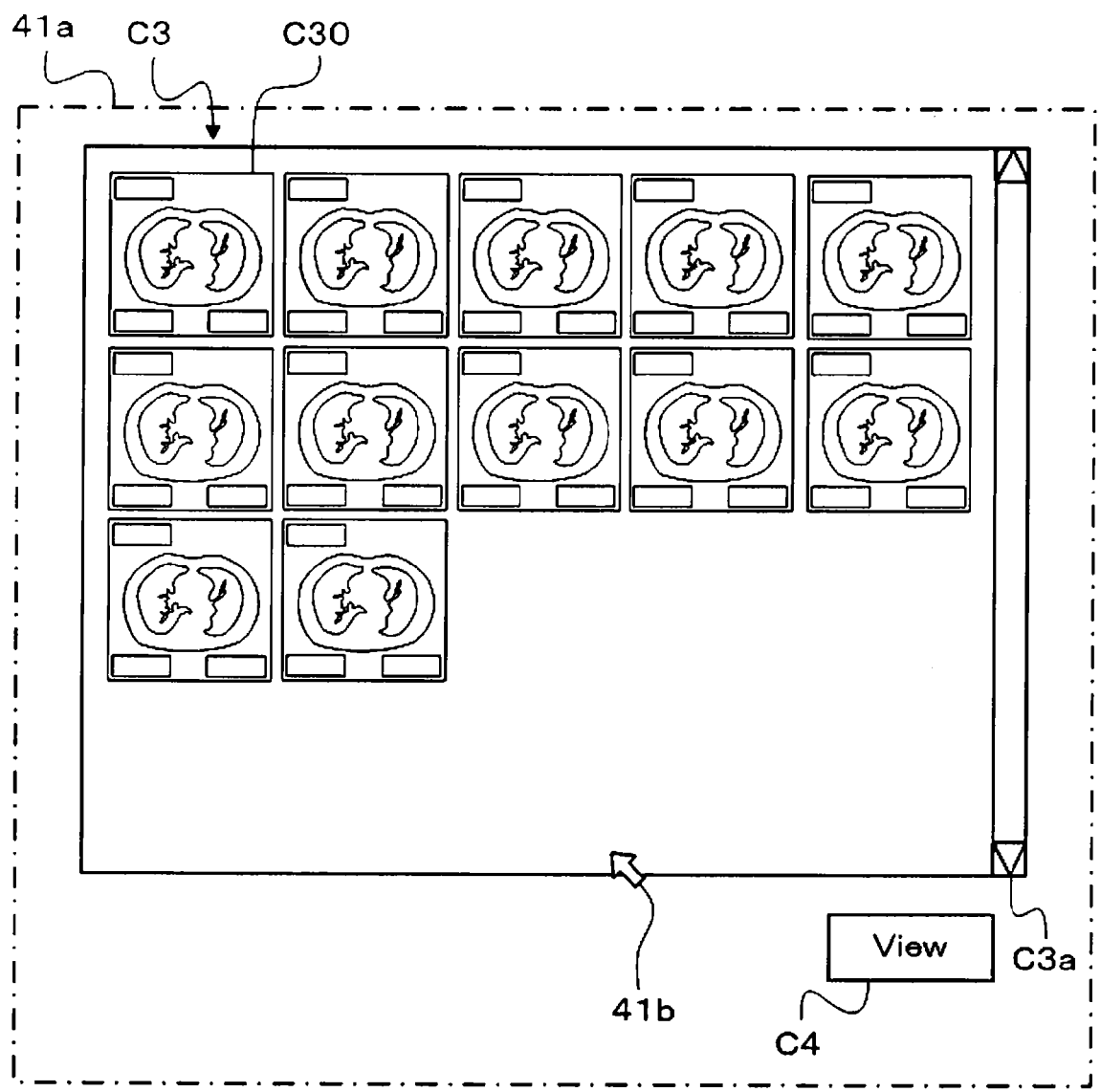
FIG. 24 is an example of an operation screen of a medical image processing apparatus according to a variation.

(Step S44)
If a selection candidate on the selection screen is clicked (Step S44: Y), the selection candidate corresponding to the position information is identified. The data-list-display controller 31 outputs the identified selection candidate and the attributes data corresponding to the selection screen to the keyword-generating part 6. Based on the attributes data and the selection candidate, the keyword-generating part 6 creates retrieval conditions for updating the data list. The keyword-generating part 6 outputs the created retrieval conditions to the retrieval part 2.
(Step S01)
The retrieval part 2 searches the data memory 1 based on the retrieval conditions. The data-list-display controller 31 updates the data list based on the retrieval results. As a result, upon receiving a drag operation performed by the operator, the rows displayed in the data list are narrowed down in real time based on the retrieval conditions. Subsequently, as long as operations by the operator continue, the medical image processing apparatus repeatedly executes the above processes. Upon detecting the end of operations, the medical image processing apparatus ends the above processes by stopping the operations of each configuration.
If none of the selection candidates on the selection screen are selected (Step S44: N), the data-list-display controller 31 deletes the selection screen displayed on the display 41. Then, the processes of step S03 onward are executed.
Furthermore, as with the medical image processing apparatus according to the first embodiment, instead of subsequently monitoring the position of the cursor and acquiring the position information, operations of acquiring the position information in response to the cursor operations may be applied. In this case, the operations related to, for example, steps S02, S43, and S44 may be replaced by processes to acquire the position information of the cursor when a click operation has been performed. In this case, if the position information of the cursor when the click operation was performed corresponds to the position information of a selection candidate on the selection screen, operations may be performed to execute the processes related to step S44.
As described above, if the operation object data are data with selection candidates, the medical image processing apparatus according to the sixth embodiment receives a drag operation and causes a selection screen with a list of selection candidates to be displayed. As a result, the operator becomes able to create retrieval conditions for the medical image processing apparatus by operating the selection screen. As a result, if the operation object data are data with selection candidates, the operator becomes able to designate retrieval conditions through simple operations.
(Variation)
As shown in FIG. 2, the above embodiments set forth examples in which the tabular data list C1 is displayed on the operation screen 41*a*. The medical image processing apparatus according to the variation displays the medical data that are the retrieval object, such as medical images, on the operation screen 41*a* together with the attributes data. By using this type of display mode, the medical image processing apparatus handles information added on image data of medical images, etc., such as annotations and comments attached to medical images, as attributes data for generating retrieval keys. The following is a description of this medical image processing apparatus with reference to FIG. 22 to FIG. 24. FIG. 22 and FIG. 23 are examples of the operation screen 41*a* of the medical image processing apparatus according to the variation. Moreover, FIG. 24 shows an example display of the operation screen 41*a* displayed on the display upon receiving an operation performed by the operator. The following description focuses on parts that are related to the generation of display screens and that are different from the abovementioned embodiments.

As shown in FIG. 22, the medical image processing apparatus according to the present embodiment displays the details of medical data (e.g., medical images) in an identifiable manner together with attributes data correlated with that medical data (e.g., patient information or imaging conditions) on the operation screen 41a. The following first describes operations of the retrieval part 2 and the data-list-display controller 31 related to the displaying of the operation screen, and then describes the screen configuration of the operation screen 41a.

(Retrieval Part 2)

When displaying the operation screen 41a, based on instructions from the keyword-generating part 6, the retrieval part 2 searches the data memory 1 and reads out a list of attributes data and a list of medical data for displaying on the operation screen 41a. Moreover, when retrieval conditions designated on the operation screen 41a are designated, the retrieval part 2 reads out the medical data corresponding to those retrieval conditions. The following is a description of operations of the retrieval part 2, including operations related to the displaying of the operation screen 41a and operations related to the displaying of medical data corresponding to the retrieval conditions.

When displaying the operation screen 41a, the retrieval part 2 receives from the keyword-generating part 6 an instruction related to the reading out of the list of attributes data and the list of medical data. In this case, the retrieval part 2 searches the data memory 1 and reads out the list of medical data and a list of attributes data correlated with each item of medical data from the data memory 1. Furthermore, in this case, it is sufficient for the retrieval part 2 to read out at least part of the medical data for displaying on the operation screen 41a. For example, if the medical data are configured by including multiple medical images, the retrieval part 2 may read out only a medical image for displaying on the operation screen 41a. In the following, partial medical data for displaying on the operation screen 41a may be referred to as "medical data for display." If retrieval conditions have been designated by the keyword-generating part 6 in addition to the instruction, the retrieval part 2 reads out only the medical data for display matching the retrieval conditions as well as a list of attributes data correlated with the medical data for display. The retrieval part 2 outputs the list of medical data for display and the list of attributes data to the data-list-display controller 31.

Next, operations related to the displaying of medical data corresponding to the retrieval conditions will be described. In addition to retrieval conditions, the retrieval part 2 receives from the keyword-generating part 6 instructions related to the reading out of medical data. In this case, the retrieval part 2 searches the data memory 1 and reads out medical data matching the retrieval conditions from the data memory 1. The retrieval part 2 outputs the medical data to the data-list-display controller 31.

(Data-List-Display Controller 31)

The data-list-display controller 31 receives a list of attributes data and a list of medical data for display from the retrieval part 2. The data-list-display controller 31 correlates the received medical data for display with the attributes data associated with the medical data for display to be groups, arranging these groups using a prescribed layout to create a data list C3. The data-list-display controller 31 incorporates the created data list C3 into a predetermined display format and creates the operation screen 41a. The data-list-display controller 31 causes the display 41 to display the created operation screen 41a. In this case, the data-list-display controller 31 associates each operation means configuring the operation screen 41a (e.g., the data list C3 as well as a data reference means C4 described later) with position information on the display 41. As a result, the data-list-display controller 31 becomes able to identify the operation object designated on the operation screen 41a based on position information on the display 41. FIG. 22 shows an example in which the operation screen 41a and the cursor 41b for designating an operation object on the operation screen 41a are displayed on the display 41. In this case, the data-list-display controller 31 preferably identifies the operation object based on the position information of the cursor 41b.

(Screen Configuration of the Operation Screen 41a)

Next, the configuration of the operation screen 41a will be described. As shown in FIG. 22, the operation screen 41a according to the variation is configured by including the data list C3 and the data reference means C4. The data list C3 is configured by including multiple regions C30. If there are too many regions C30 to display all of the regions C30 in a single screen, as shown in FIG. 22, a scrollbar C3a may be displayed.

Here, we will refer to FIG. 23. FIG. 23 is a diagram for describing detailed configurations of the regions C30. As shown in FIG. 23, the regions C30 are configured by including medical data for display C31, patient information C32, imaging conditions C33, and management information C34. The patient information C32, the imaging conditions C33, and the management information C34 correspond to attributes data. The patient information C32 is attributes data indicating information on a patient, such as the name and age of the patient. Moreover, the imaging conditions C33 are attributes data related to the conditions under which medical data were acquired, such as examination date, diagnosed site, and resolution. Moreover, the management information C34 shows the management state of the corresponding medical data. For example, if the medical data stored in the medical image processing apparatus are uniformly managed in a server connected to the apparatus via a network, information regarding whether or not medical data have been transferred to the server may be managed using this management information C34. Moreover, on the medical data for display C31, annotations C351 attached to the corresponding medical data and comments C352 included in the annotations C351 may be displayed as attributes data. The patient information C32, the imaging conditions C33, the management information C34, and the comments C352 are displayed to be selected as operation objects of the cursor 41b, and these items of information correspond to the attributes data displayed in the region C11 in FIG. 2. In other words, in the medical image processing apparatus according to the variation, when there is an operation by the cursor 41b on a region in which these items of information are displayed, as in the abovementioned embodiments, retrieval conditions are generated. Furthermore, in the above, the attributes data associated with the medical data have been described by dividing them into the patient information C32, the imaging conditions C33, and the management information C34, but these categorizations may be changed as needed.

The data reference means C4 is an operation means for displaying medical data. When the data reference means C4 is operated while any of the regions C30 in the data list C3 is selected, the retrieval part 2 reads out the medical data corresponding to the selected region C30. The data-list-display controller 31 causes the display 41 to display the medical data that have been read out. As a result, the operator becomes able to identify and refer to desired medical data based on the data list C3.

As described above, the medical image processing apparatus of the variation allows medical data that are the retrieval object, such as medical images, to be displayed on the operation screen 41a together with attributes data. Displaying in such a state allows the medical image processing apparatus to handle information added on image data (medical images, etc), such as annotations and comments attached to medical images, as attributes data for generating a retrieval key.

The cursor operations described in the above embodiments are not limited to operations performed using a mouse. Mouse operations may be replaced as needed by, for example, operations using a touch panel or pen inputs using a stylus. In such a case, it is preferable to change the operations of the operation part 42 and the cursor controller 32 as needed in accordance with the methods of operation and to associate them with the click operations and drag operations described above. For example, in the case of operations using a touch panel, the display 41 is preferably configured by being combined with the operation part 42. In this case, the display 41 receives touch operations and outputs the operation information to the cursor controller 32. The cursor controller 32 is preferably configured to identify, based on the operation information, the position information on the display 41 where the touch operation was performed.

Several embodiments of the present invention have been described, but these embodiments have been presented as examples and are not intended to limit the scope of the invention. These new embodiments may be implemented in various other modes, and various omissions, substitutions, and changes may be made within the scope of the substance of the invention. These embodiments and modifications thereof are included in the scope and substance of the invention and are also included in a scope equivalent to that described in the scope of patent claims.

EXPLANATION OF SYMBOLS

1: Data memory
2: Retrieval part
3: Display controller
31: Data-list-display controller
32: Cursor controller
33: Operation-details analyzer
34: Format-converting part
35: Format-data memory
36: Guide-display controller
37: Selection-screen display controller
4: UI
41: Display
41a: Data list
41b: Cursor
42: Operation part
5: Attributes-data analyzer
6: Keyword-generating part
7: Data-type memory

What is claimed is:
1. A medical image processing apparatus comprising:
a display;
a data memory that stores medical data associated with attributes data represented as one or a plurality of unit of data;
circuitry implementing
a data-list-display controller that associates a data list presenting the attributes data in a list with position information on the display, causing the display to display the data list,
a cursor controller that causes the display to display a cursor and that, upon receiving an instruction, changes the position at which the cursor is displayed and outputs the position information thereof,
an attributes-data analyzer that identifies units of data within the attributes data based on the position information,
wherein the circuitry further implements
an operation-details analyzer that, in response to a change of the position information, detects the direction of movement of the cursor in either a first direction along a predetermined first axis or a second direction opposite to the first direction, as well as the amount of movement of the cursor along the first axis,
a keyword generator that, in conjunction with changes in the position information, selects a range of units of data within the attributes data and generates a retrieval key based on the units of data corresponding to the selected range, and
a retriever that searches the data memory using the retrieval key,
wherein the attributes-data analyzer receives the position information, identifies the attributes data corresponding to the position information from within the data list as operation object data, and divides the operation object data into the units of data,
when the amount of movement in the first direction is shorter than a predetermined distance, the keyword generator generates a retrieval key using only head data composed of the unit of data positioned at a beginning of the operation object data, and each time the amount of movement in a first direction increases by the equivalent of the first unit distance, the keyword generator extracts plural units of data sequentially from the head data and combines the extracted plural units of data which include the head data to generate a new retrieval key, and
wherein the data-list-display controller, based on the new retrieval key, updates and displays the data list.

2. The medical image processing apparatus according to claim 1, wherein
when the amount of movement in the second direction exceeds the first unit distance, the keyword generator generates a retrieval key for removing the attributes data including the operation object data from a retrieval object, and each time the amount of movement in the second direction increases by the equivalent of the first unit distance, the keyword generator identifies the units of data sequentially from an end to a beginning of the operation object data and generates a retrieval key for removing the attributes data including partial data in which the identified units of data have been deleted from the operation object data from the retrieval object.

3. The medical image processing apparatus according to claim 1, wherein
the operation-details analyzer receives the position information and also detects both the direction of movement of the cursor in either a third direction along a predetermined second axis different from the first axis or a fourth direction opposite to the third direction, as well as the amount of movement of the cursor along the second axis, and each time the amount of movement in the third direction increases by the equivalent of a predetermined second unit distance, the keyword generator adds to the retrieval key another retrieval key in which a prescribed number of units of tail data positioned at the end of the retrieval key have been changed to the units of data positioned next to the tail data in any predefined sequence of values that the units of data configuring the operation object data may take, and each time the amount of movement in the fourth direction increases by the equivalent of the second unit distance, the keyword generator adds to the retrieval key another retrieval key in which the tail data positioned at the end of the retrieval key has been changed to the units of data positioned next to the tail data in the opposite direction in the sequence.

4. The medical image processing apparatus according to claim 3, wherein each item of the attributes data is associated with at least one of the first direction, the second direction, the third direction, and the fourth direction, and the keyword generator generates the retrieval key only when the cursor is moved in a direction associated with the operation object data.

5. The medical image processing apparatus according to claim 1, further comprising:

a format-data memory that, for the attributes data that may be defined with a plurality of formats in which the sequence of the units of data has been switched, stores format data associating each item of attributes data with formats; and a format converter implemented by the circuitry that, based on the format data, converts the attributes data that may be defined with the plurality of formats into any one of the predefined formats from among the plurality of formats, wherein when the attributes data that may be defined with the plurality of formats is included in the data list, the data-list-display controller causes the format converter to convert the format of the attributes data and displays the attribute data on the display.

6. The medical image processing apparatus according to claim 1, wherein the data-list-display controller divides a single field displaying the attributes data in the data list into a plurality of regions, and associates the attributes data with each region, and the attributes-data analyzer receives the position information, identifies the region associated with the position information from within the data list, and identifies the attributes data associated with the region as the operation object data.

7. The medical image processing apparatus according to claim 6, further comprising:

a guide-display controller implemented by the circuitry that causes the display to visibly display the directions associated with the operation object data.

8. The medical image processing apparatus according to claim 1 wherein when the operation object data is the attributes data that may be extracted using only any one of two or more predetermined units of the units of data, the keyword generator receives a movement of the cursor, switches to the generation of the retrieval key, displays any of the two or more units of data in a selectable manner, and when any of the two or more units of data is selected, generates the retrieval key based on the selected unit of data.

9. The medical image processing apparatus according to claim 1, wherein the data-list-display controller correlates details of at least part of the medical data associated with the attributes data with the attributes data to make them identifiable, and displays the details as the data list.

\* \* \* \* \*